(12) United States Patent
Belson

(10) Patent No.: US 10,799,680 B2
(45) Date of Patent: Oct. 13, 2020

(54) INTRAVENOUS CATHETER INSERTION AND BLOOD SAMPLE DEVICES AND METHOD OF USE

(71) Applicant: Vascular Pathways, Inc., Los Altos, CA (US)

(72) Inventor: Amir Belson, Los Altos, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 119 days.

(21) Appl. No.: 16/138,523

(22) Filed: Sep. 21, 2018

(65) Prior Publication Data

US 2019/0022358 A1   Jan. 24, 2019

Related U.S. Application Data

(63) Continuation of application No. 15/692,915, filed on Aug. 31, 2017, now Pat. No. 10,086,171, which is a
(Continued)

(51) Int. Cl.
*A61B 5/00* (2006.01)
*A61M 25/06* (2006.01)
(Continued)

(52) U.S. Cl.
CPC ..... *A61M 25/0606* (2013.01); *A61B 5/15003* (2013.01); *A61B 5/1535* (2013.01);
(Continued)

(58) Field of Classification Search
CPC ........ A61B 5/150656; A61B 5/150992; A61B 5/1535; A61B 5/15003; A61B 5/150351;
(Continued)

(56) References Cited

U.S. PATENT DOCUMENTS 2,211,975 A    8/1940  Hendrickson
2,259,488 A   10/1941  Raiche
(Continued)

FOREIGN PATENT DOCUMENTS

AU    691141 B2   5/1998
AU    710967 B2   9/1999
(Continued)

OTHER PUBLICATIONS

CN 201580022407.7 filed Nov. 2, 2016 Office Action dated Sep. 16, 2019.
(Continued)

*Primary Examiner* — Max F Hindenburg
(74) *Attorney, Agent, or Firm* — Rutan & Tucker LLP

(57) ABSTRACT

A catheter insertion device includes a handle, a needle, a guide wire, and a catheter. The handle may have a proximal region and a distal region. The distal region may include a slot between a top extension and a bottom extension, which extends through a distal end. The needle may have a proximal end positioned in the proximal region and a distal end extending from the distal region. The guide wire may have a proximal end positioned in the proximal region of the handle and a distal end positioned in a lumen of the needle. The catheter may be positioned coaxially over the needle with a proximal end connected to a catheter hub. The catheter hub may be slidably disposed in the slot to enable movement from a first position in the distal region to a second position distal of the distal region.

18 Claims, 27 Drawing Sheets

Related U.S. Application Data continuation of application No. 14/876,735, filed on Oct. 6, 2015, now Pat. No. 9,757,540, which is a continuation of application No. 14/174,071, filed on Feb. 6, 2014, now Pat. No. 9,675,784, which is a continuation of application No. 12/598,053, filed as application No. PCT/US2008/062954 on May 7, 2008, now Pat. No. 8,721,546.

(60) Provisional application No. 60/916,552, filed on May 7, 2007, provisional application No. 60/916,553, filed on May 7, 2007.

(51) Int. Cl.

| | |
|---|---|
| *A61B 5/15* | (2006.01) |
| *A61B 5/154* | (2006.01) |
| *A61M 25/01* | (2006.01) |
| *A61M 25/09* | (2006.01) |
| *A61B 17/34* | (2006.01) |
| *A61B 5/153* | (2006.01) |

(52) U.S. Cl.
CPC ........ *A61B 5/1545* (2013.01); *A61B 5/15074* (2013.01); *A61B 5/150389* (2013.01); *A61B 5/150503* (2013.01); *A61B 5/150656* (2013.01); *A61B 5/150992* (2013.01); *A61B 17/3415* (2013.01); *A61B 17/3421* (2013.01); *A61M 25/0105* (2013.01); *A61M 25/0631* (2013.01); *A61M 25/09* (2013.01); *A61M 25/09041* (2013.01); *A61B 5/150351* (2013.01); *A61M 2025/09133* (2013.01); *A61M 2025/09141* (2013.01); *A61M 2025/09175* (2013.01)

(58) Field of Classification Search
CPC ........ A61B 5/150389; A61B 5/150503; A61B 5/15074; A61B 5/1545; A61B 17/3421; A61B 17/3415; A61M 25/0606; A61M 25/0105; A61M 25/0631; A61M 25/09; A61M 25/09041; A61M 2025/09141; A61M 2025/09175

See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vaillancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |

(56) References Cited

U.S. PATENT DOCUMENTS

| | | |
|---|---|---|
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Naughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |

(56) References Cited

U.S. PATENT DOCUMENTS

| | | |
|---|---|---|
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |

(56) References Cited

U.S. PATENT DOCUMENTS

| | | |
|---|---|---|
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |

(56) References Cited

U.S. PATENT DOCUMENTS

| | | |
|---|---|---|
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |

(56) References Cited

U.S. PATENT DOCUMENTS

| | | |
|---|---|---|
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| 9,522,254 B2 | 12/2016 | Belson |
| 9,545,495 B2 | 1/2017 | Goral et al. |
| 9,554,817 B2 | 1/2017 | Goldfarb et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,384,039 B2 | 8/2019 | Ribelin et al. |
| 10,426,931 B2 | 10/2019 | Blanchard et al. |
| 10,493,262 B2 | 12/2019 | Tran et al. |
| 10,525,236 B2 | 1/2020 | Belson |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |

(56) References Cited

U.S. PATENT DOCUMENTS

| | | |
|---|---|---|
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0036331 A1 | 2/2010 | Sen |
| 2010/0056910 A1 | 3/2010 | Yanuma |
| 2010/0087787 A1 | 4/2010 | Woehr et al. |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0106959 A1 | 4/2016 | Woehr |

(56) References Cited

U.S. PATENT DOCUMENTS

| | | |
|---|---|---|
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 2150304 A2 | 2/2010 |
| EP | 2272432 A1 | 1/2011 |
| EP | 2569046 A1 | 3/2013 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| WO | 83/01575 A1 | 5/1983 |
| WO | 1983001575 A1 | 5/1983 |
| WO | 1992013584 A1 | 8/1992 |
| WO | 92/22344 A1 | 12/1992 |
| WO | 1992022344 A1 | 12/1992 |
| WO | 1995011710 A1 | 5/1995 |
| WO | 95/19193 A1 | 7/1995 |
| WO | 1995019193 A1 | 7/1995 |
| WO | 95/23003 A1 | 8/1995 |
| WO | 1995023003 A1 | 8/1995 |
| WO | 96/32981 A1 | 10/1996 |
| WO | 1996032981 A1 | 10/1996 |
| WO | 1996040359 A1 | 12/1996 |
| WO | 97/05912 A2 | 2/1997 |
| WO | 1997005912 A2 | 2/1997 |
| WO | 97/21458 A1 | 6/1997 |
| WO | 1997021458 A1 | 6/1997 |
| WO | 1997045151 A1 | 12/1997 |
| WO | 98/24494 A1 | 6/1998 |
| WO | 1998024494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 2001007103 A1 | 2/2001 |
| WO | 01/26725 A1 | 4/2001 |
| WO | 2002041932 A2 | 5/2002 |
| WO | 02/066093 A2 | 8/2002 |
| WO | 03/11381 A1 | 2/2003 |
| WO | 03/043686 A1 | 5/2003 |
| WO | 03/43686 A1 | 5/2003 |
| WO | 03/47675 A2 | 6/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008137956 A1 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |

(56) References Cited

FOREIGN PATENT DOCUMENTS

| WO | 2012174109 | A1 | 12/2012 |
|---|---|---|---|
| WO | 2013119557 | A1 | 8/2013 |
| WO | 2013126446 | A1 | 8/2013 |
| WO | 2013187827 | A1 | 12/2013 |
| WO | 2014006403 | A1 | 1/2014 |
| WO | 2014029424 | A1 | 2/2014 |
| WO | 2014074417 | A2 | 5/2014 |
| WO | 2014081942 | A1 | 5/2014 |
| WO | 2014/123848 | A1 | 8/2014 |
| WO | 2014120741 | A1 | 8/2014 |
| WO | 2014133617 | A1 | 9/2014 |
| WO | 2014140257 | A1 | 9/2014 |
| WO | 2014140265 | A1 | 9/2014 |
| WO | 2014/165783 | A1 | 10/2014 |
| WO | 2014158908 | A1 | 10/2014 |
| WO | 2014182421 | A1 | 11/2014 |
| WO | 2014197656 | A1 | 12/2014 |
| WO | 2014204593 | A1 | 12/2014 |
| WO | 2015017136 | A1 | 2/2015 |
| WO | 2015024904 | A1 | 2/2015 |
| WO | 2015035393 | A1 | 3/2015 |
| WO | 2015058136 | A1 | 4/2015 |
| WO | 15108913 | A1 | 7/2015 |
| WO | 2015/168655 | A2 | 11/2015 |
| WO | 15164912 | A1 | 11/2015 |
| WO | 2016/037127 | A1 | 3/2016 |
| WO | 16178974 | A1 | 11/2016 |
| WO | 2018/049413 | A1 | 3/2018 |
| WO | 2019173641 | A1 | 9/2019 |

OTHER PUBLICATIONS

EP 19181963.0 filed Jun. 24, 2019 Extended European Search Report dated Jul. 16, 2019.
U.S. Appl. No. 15/154,384, filed May 13, 2016 Non-Final Office Action dated Jun. 28, 2019.
U.S. Appl. No. 15/608,802, filed May 30, 2017 Non-Final Office Action dated Jun. 6, 2019.
U.S. Appl. No. 15/702,537, filed Sep. 12, 2017 Notice of Allowance dated Jul. 31, 2019.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/951,954, filed Apr. 12, 2018 Non-Final Office Action dated Nov. 4, 2019.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.
U.S. Appl. No. 14/876,735, filed Oct. 6, 2015 Non-Final Office Action dated Mar. 30, 2017.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Restriction Requirement dated Jan. 3, 2018.
U.S. Appl. No. 15/377,880, filed Dec. 13, 2016 Non-Final Office Action dated May 14, 2018.
U.S. Appl. No. 15/481,773, filed Apr. 7, 2017 Non-Final Office Action dated Jun. 29, 2018.
U.S. Appl. No. 15/692,915, filed Aug. 31, 2017 Non-Final Office Action dated Jan. 29, 2018.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
Notice of allowance dated Jun. 10, 2015 for U.S. Appl. No. 11/577,491.

(56) References Cited

OTHER PUBLICATIONS

Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
EP 12782187.4 filed Sep. 10, 2013 Office Action dated Nov. 28, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 14/846,387, filed Sep. 4, 2015 Notice of Allowance dated Oct. 29, 2018.
U.S. Appl. No. 14/866,441, filed Sep. 25, 2015 Notice of Allowance dated Oct. 17, 2018.
U.S. Appl. No. 15/154,808, filed May 13, 2016 Advisory Action dated Oct. 26, 2018.
U.S. Appl. No. 15/377,880, filed Dec. 13, 2016 Final Office Action dated Oct. 19, 2018.
U.S. Appl. No. 15/481,773, filed Apr. 7, 2017 Final Office Action dated Jan. 10, 2019.
U.S. Appl. No. 15/702,537, filed Sep. 12, 2017 Non-Final Office Action dated Nov. 29, 2018.
CN 201580022407.7 filed Nov. 2, 2016 Office Action dated Jan. 31, 2019.
EP 07783404.2 filed Jan. 19, 2009 Office Action dated Apr. 16, 2019.
EP 16797047.4 filed Dec. 6, 2017 Supplemental European Search Report dated Jan. 9, 2019.
JP 2016-563441 filed Oct. 19, 2016 Office Action dated Jan. 25, 2019.
JP 2018-039302 filed Mar. 6, 2018 Office Action dated Feb. 20, 2019.
U.S. Appl. No. 14/585,800, filed Dec. 30, 2014 Notice of Allowance dated Feb. 25, 2019.
U.S. Appl. No. 15/154,384, filed May 13, 2016 Restriction Requirment dated Jan. 25, 2019.
U.S. Appl. No. 15/154,808, filed May 13, 2016 Notice of Allowance dated Apr. 16, 2019.
U.S. Appl. No. 15/702,537, filed Sep. 12, 2017 Final Office Action dated Mar. 8, 2019.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.

(56) References Cited

OTHER PUBLICATIONS

CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
JP 2016-107046 filed May 30, 2016 Office Action dated Jul. 28, 2016.
JP 2016-107046 filed May 30, 2016 Office Action dated Nov. 7, 2017.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
U.S. Appl. No. 15/154,384, filed May 13, 2016 Final Office Action dated Nov. 27, 2019.
U.S. Appl. No. 15/727,528, filed Oct. 6, 2017 Final Office Action dated Jan. 28, 2020.
U.S. Appl. No. 15/862,380, filed Jan. 4, 2018 Restriction Requirement dated Dec. 23, 2019.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,954, filed Apr. 12, 2018 Notice of Allowance dated Feb. 23, 2020.
U.S. Appl. No. 29/654,527, filed Jun. 25, 2018 Restriction Requirement dated Mar. 10, 2020.

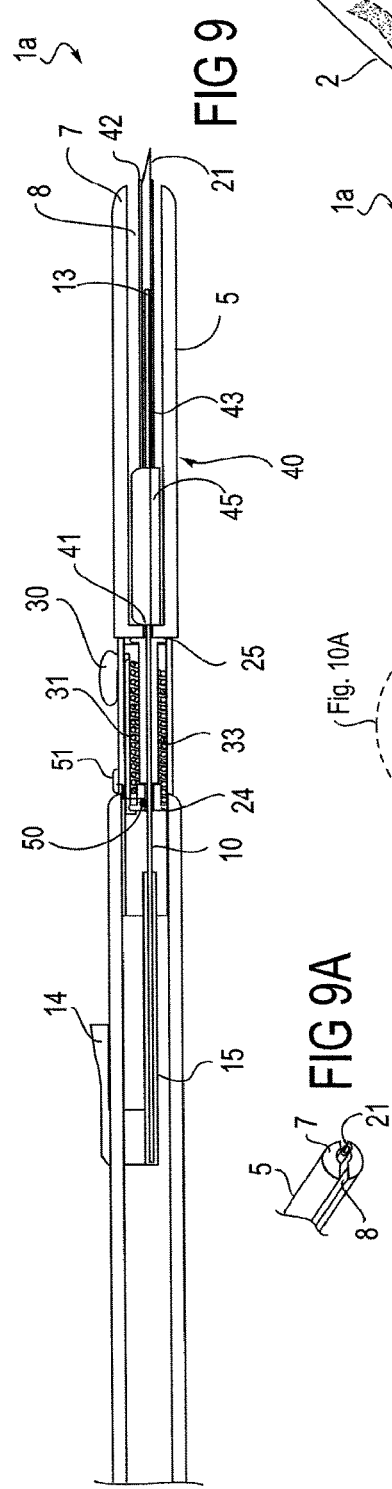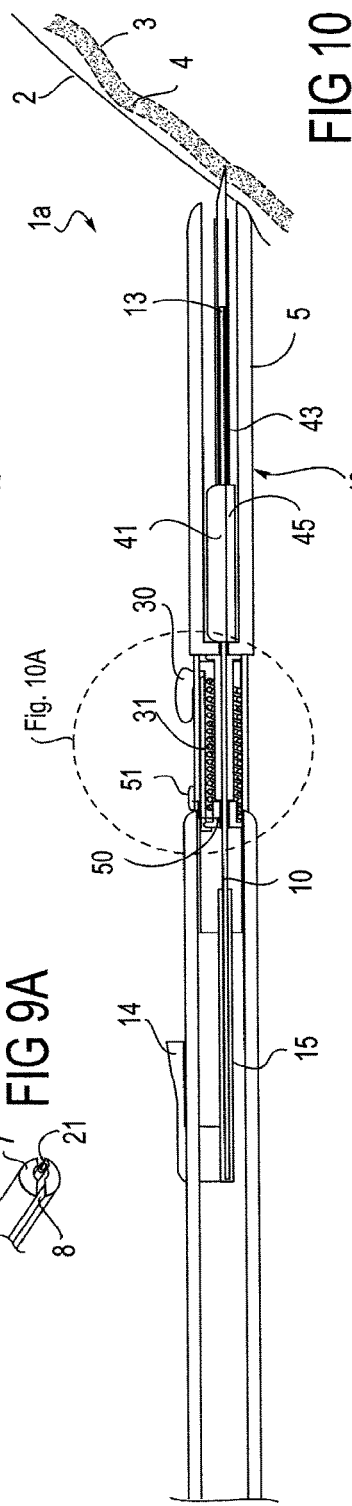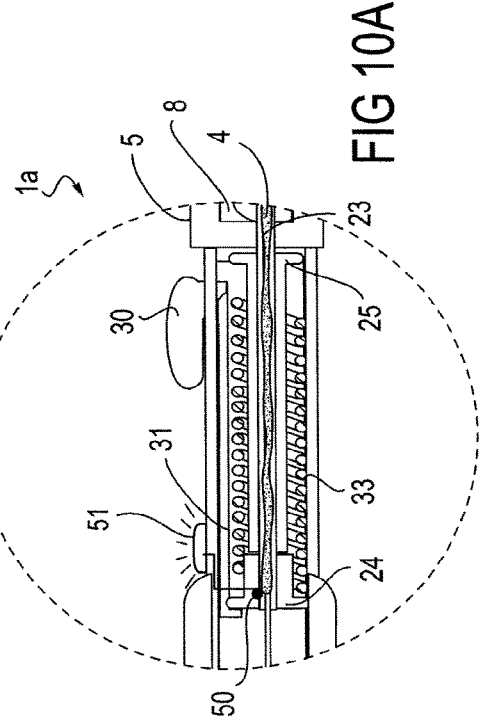

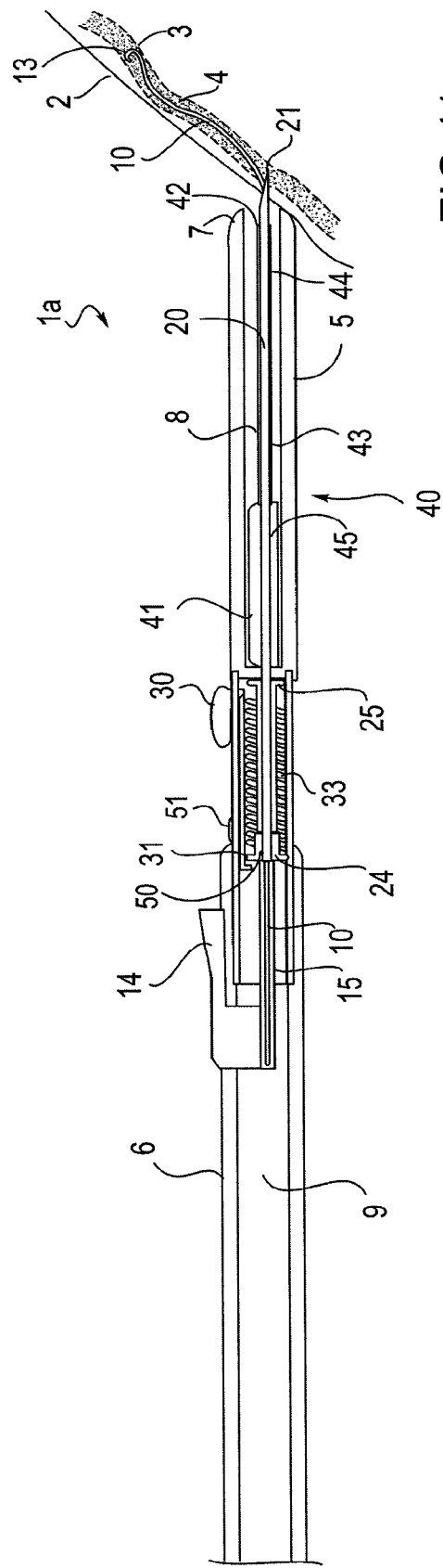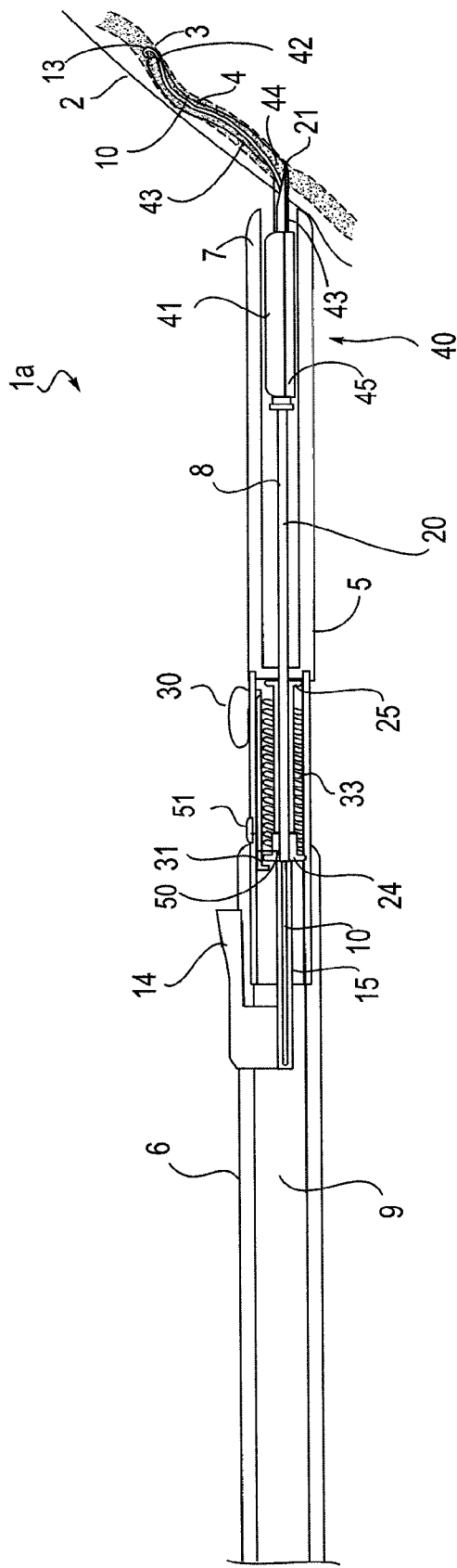

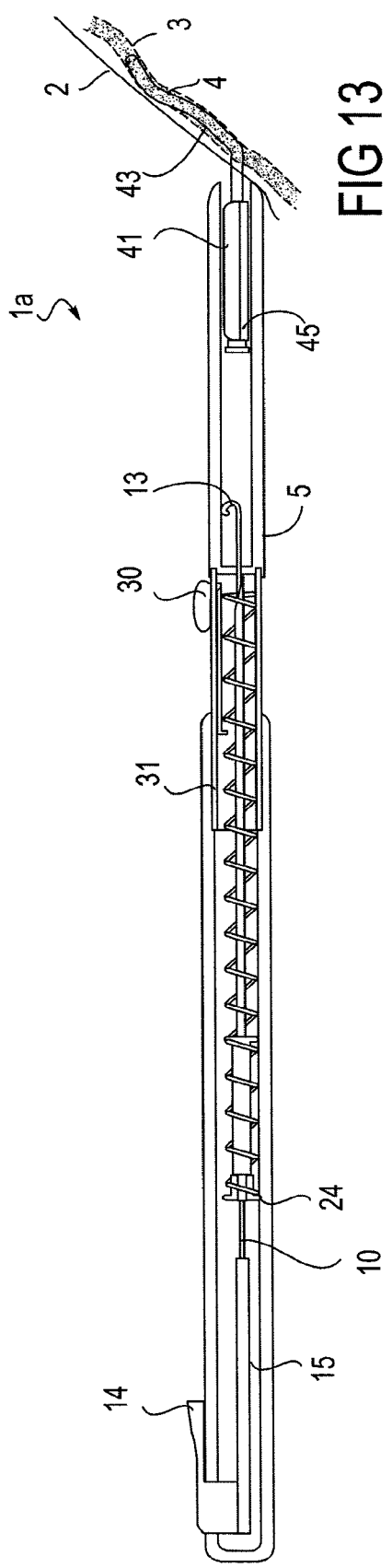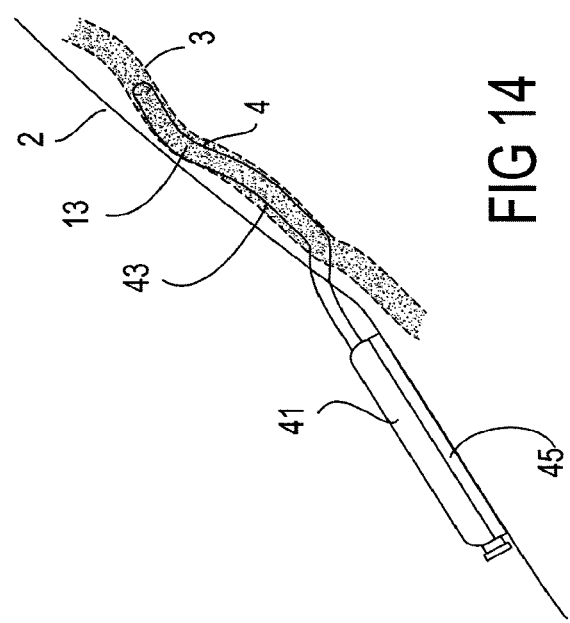

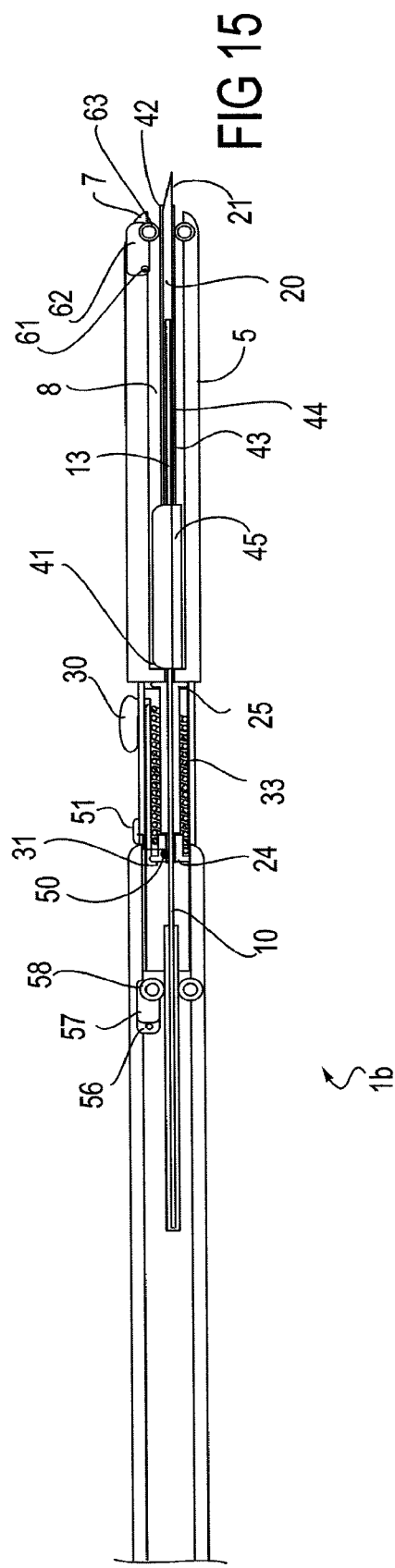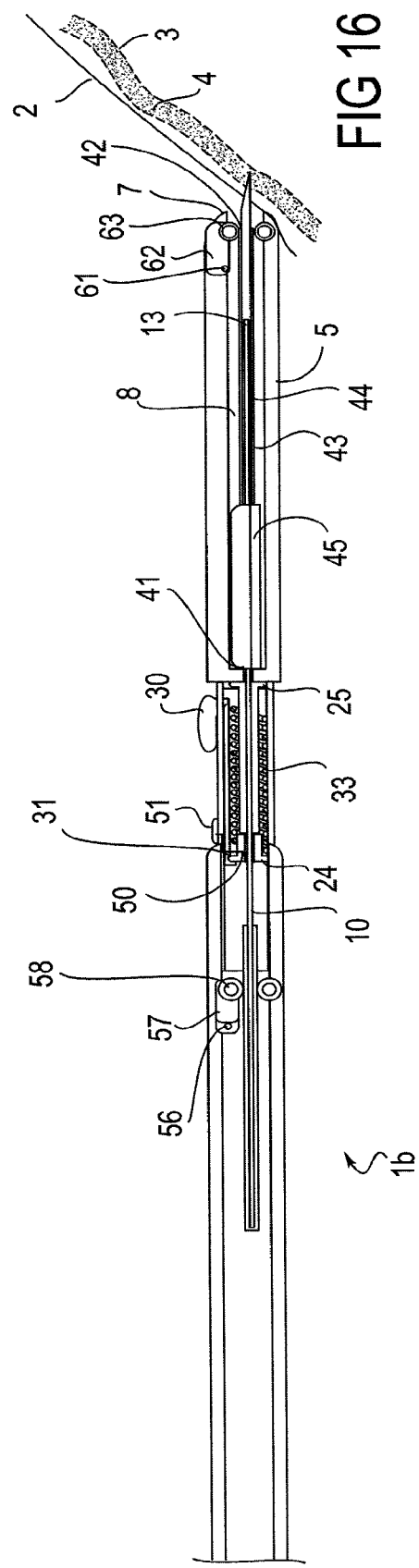

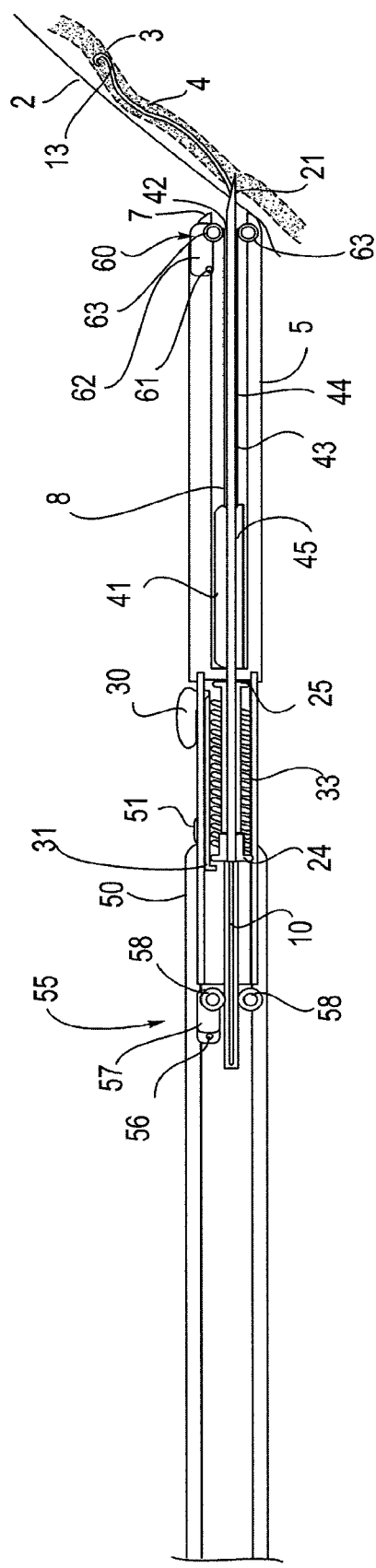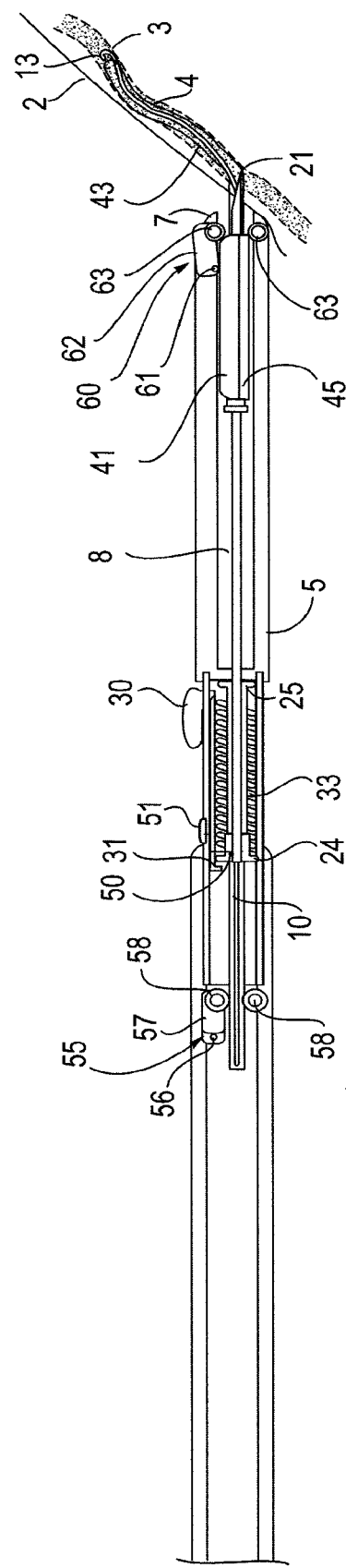

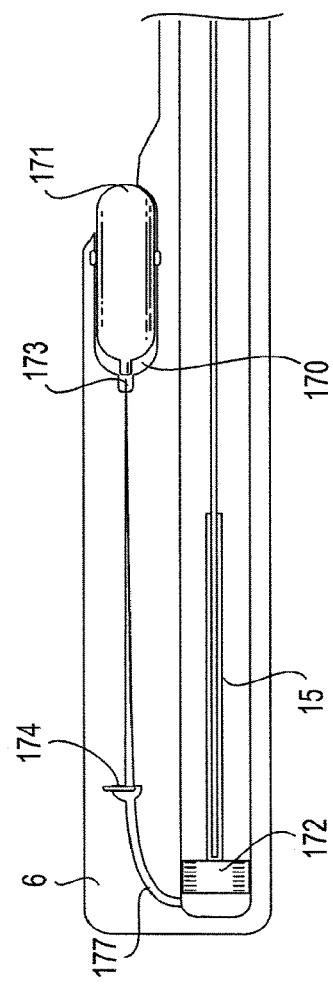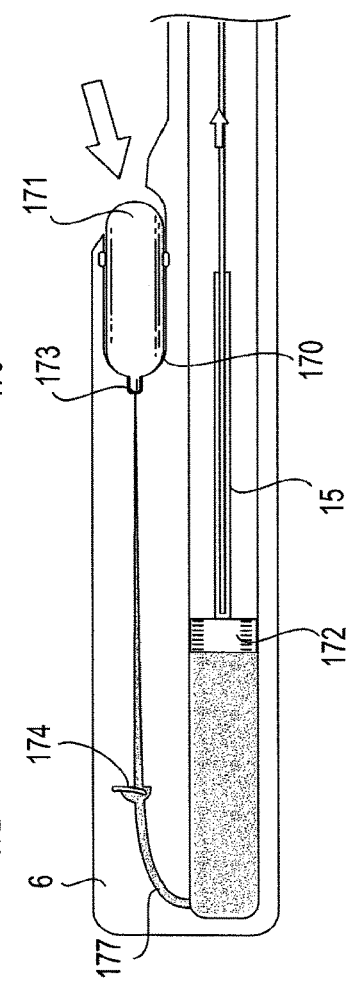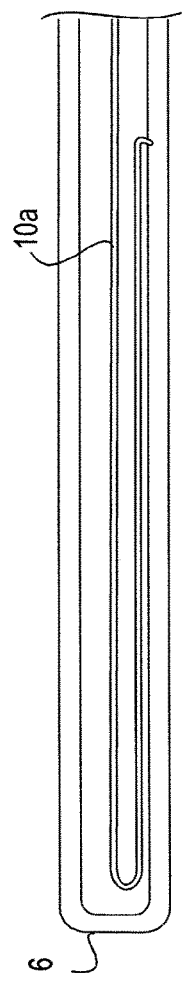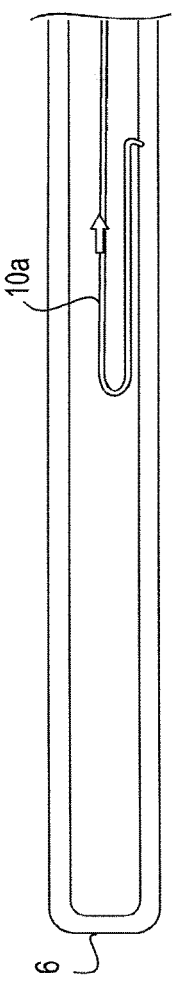
FIG 21A
FIG 21B
FIG 22A
FIG 22B

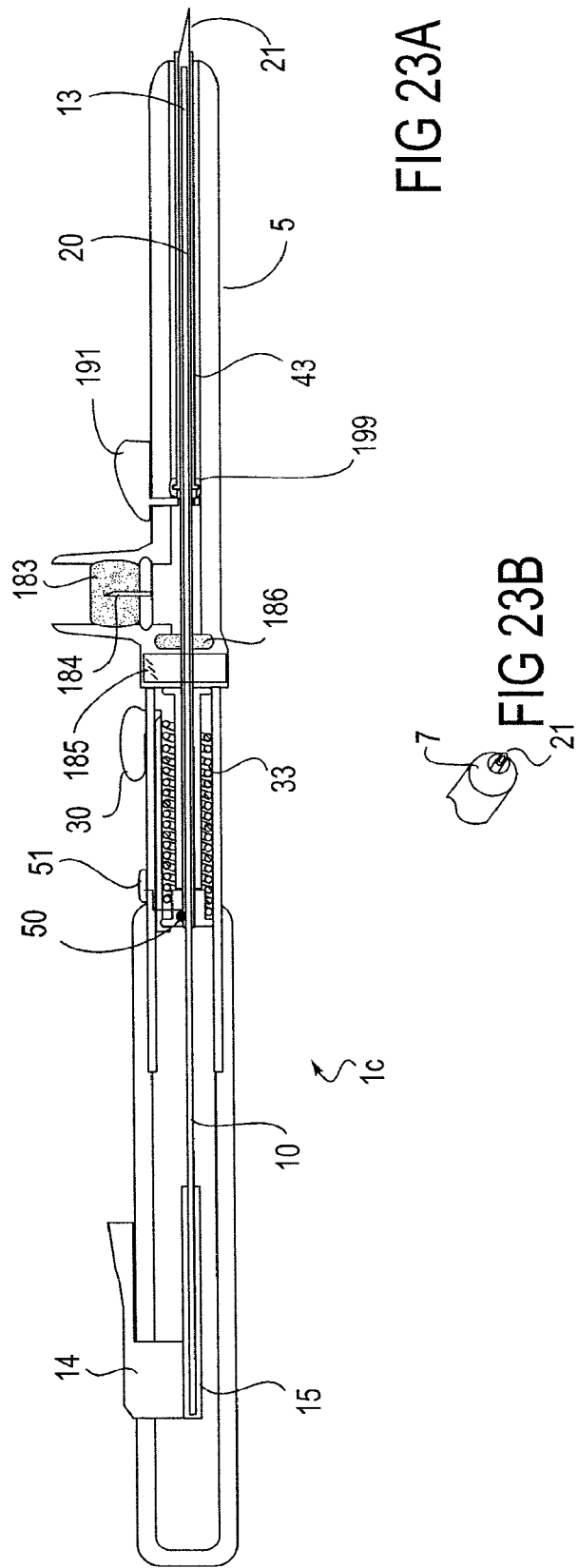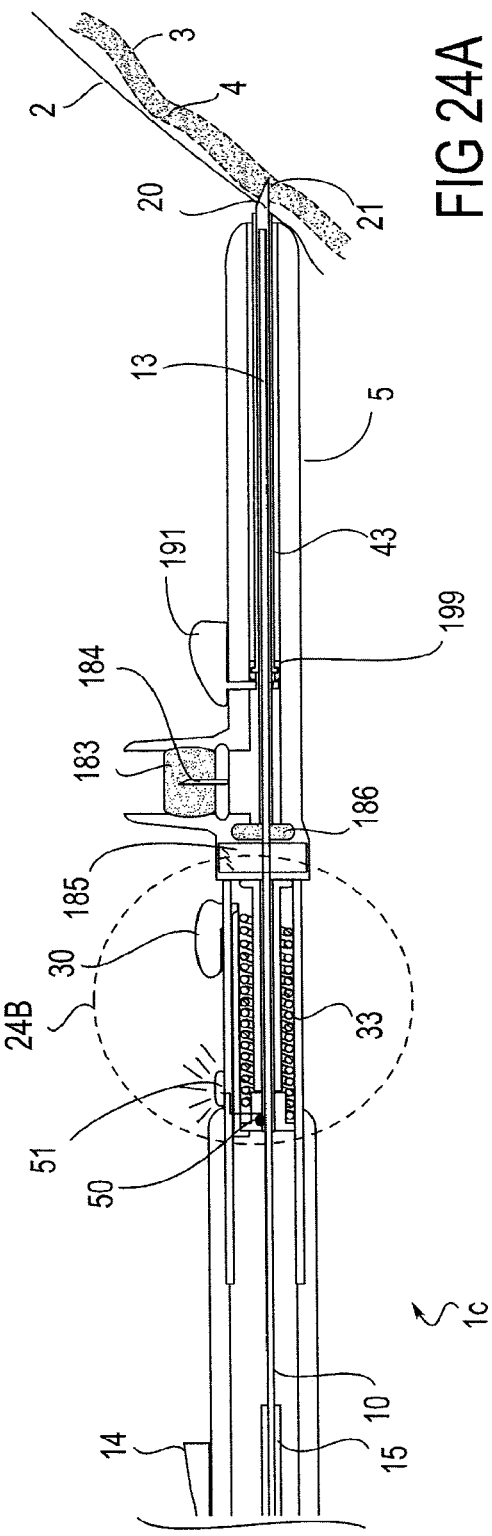

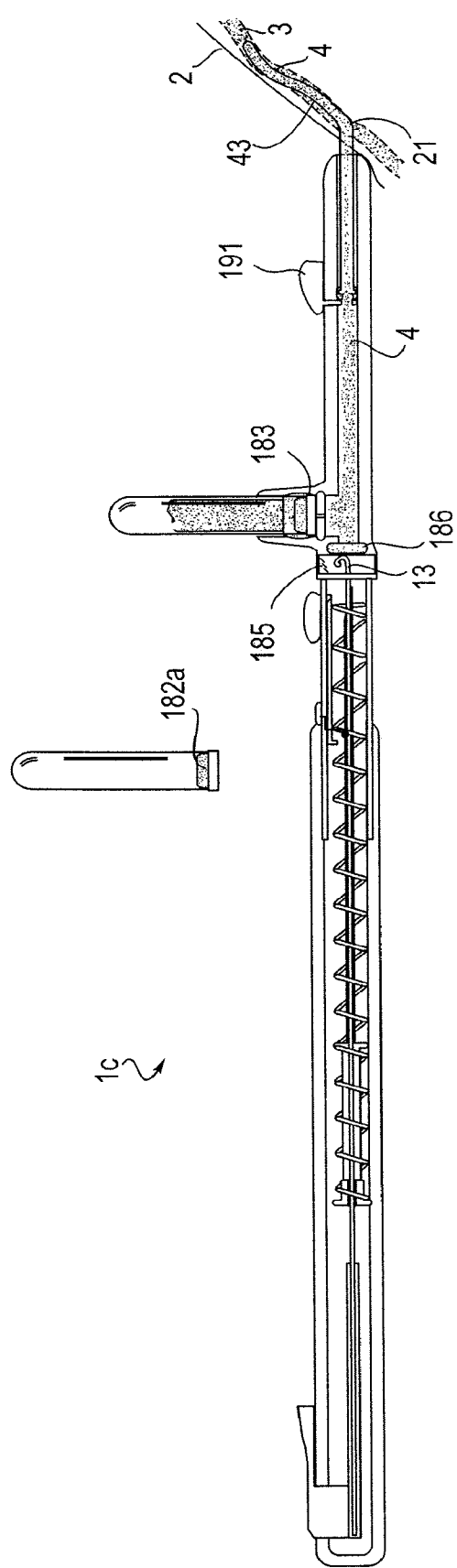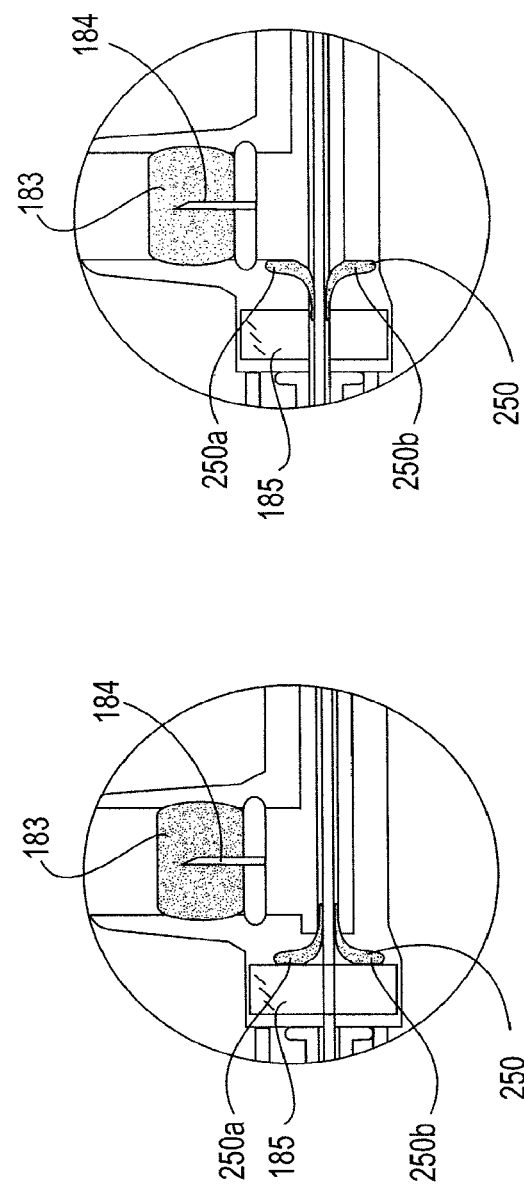

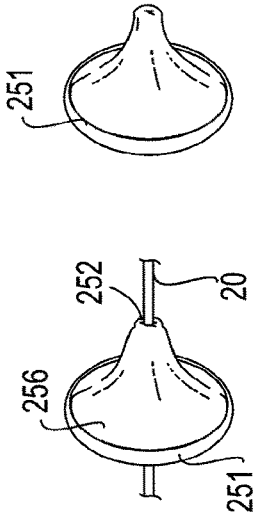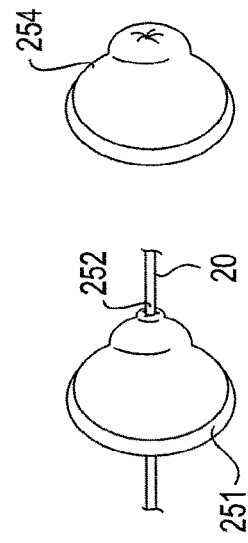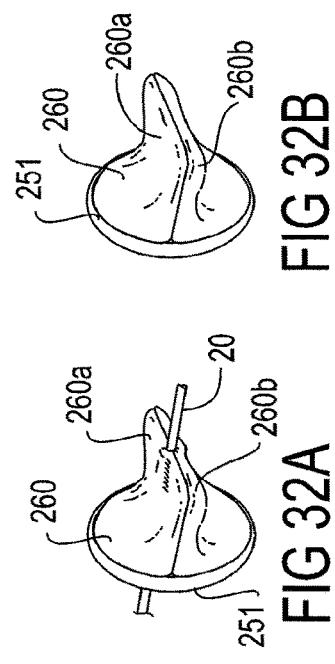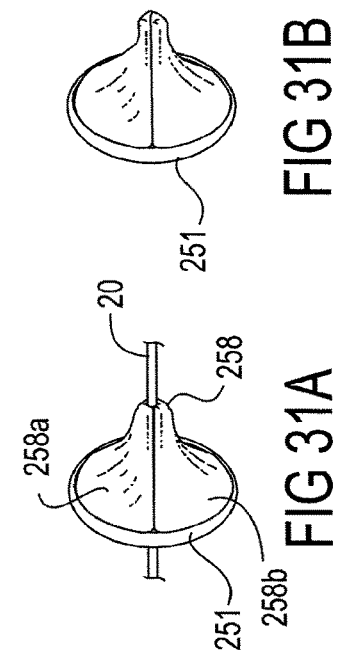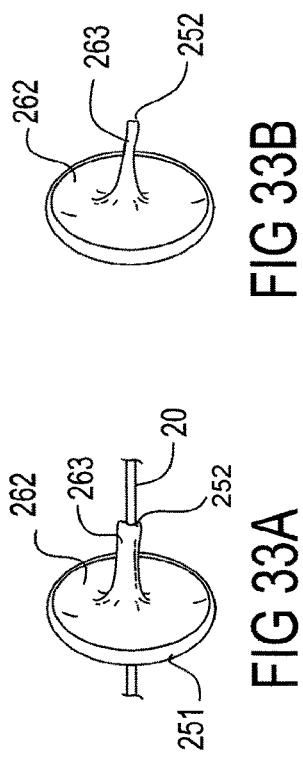

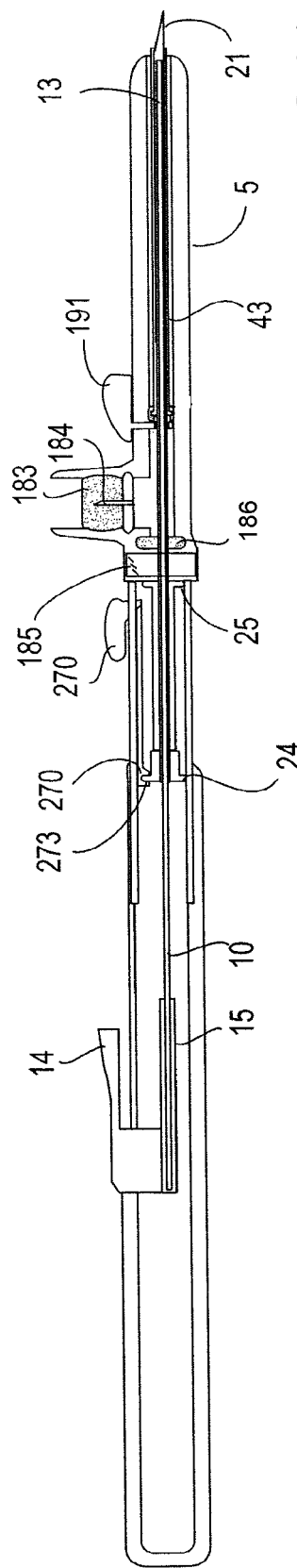
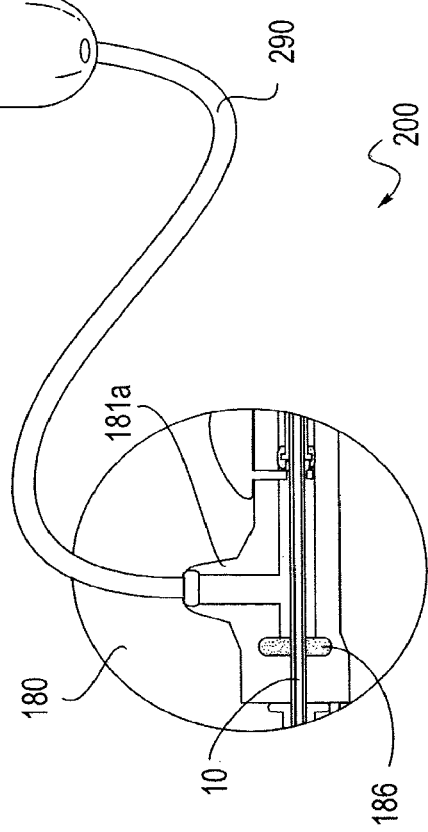
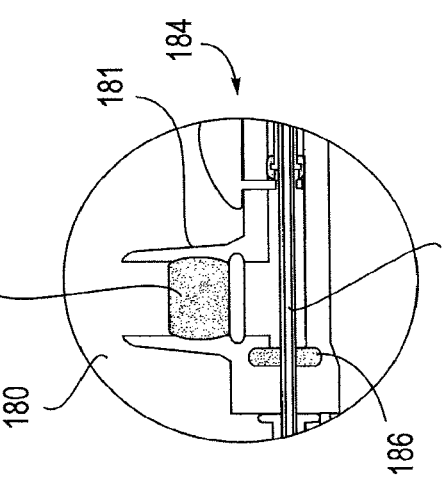
FIG 34
FIG 35
FIG 36

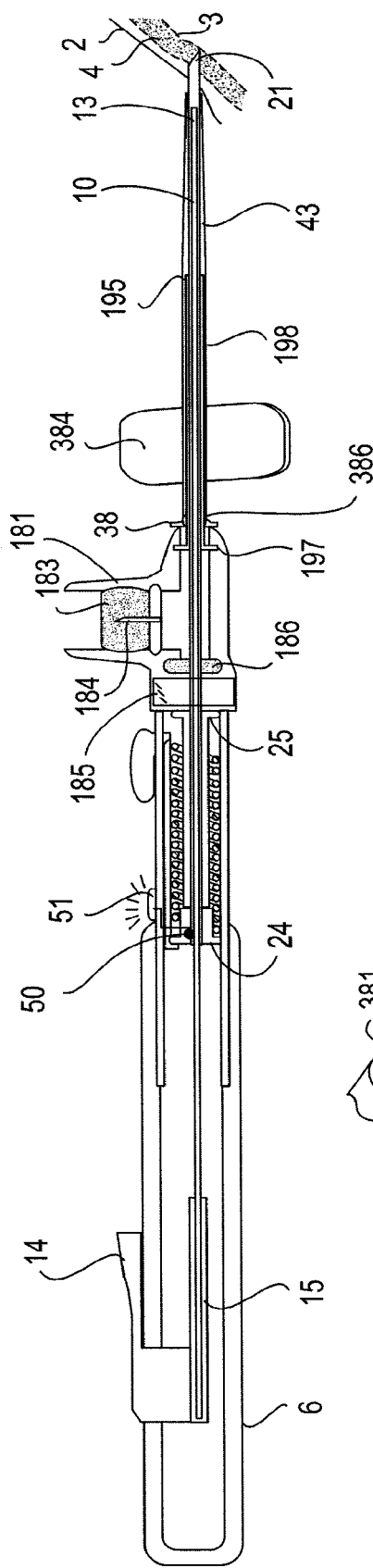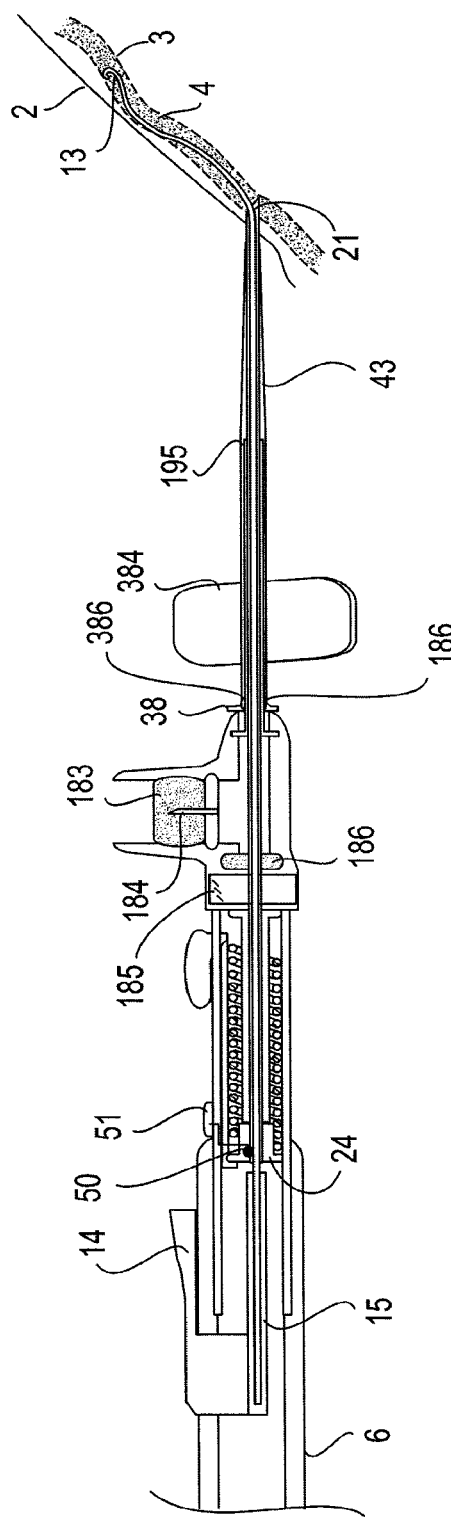

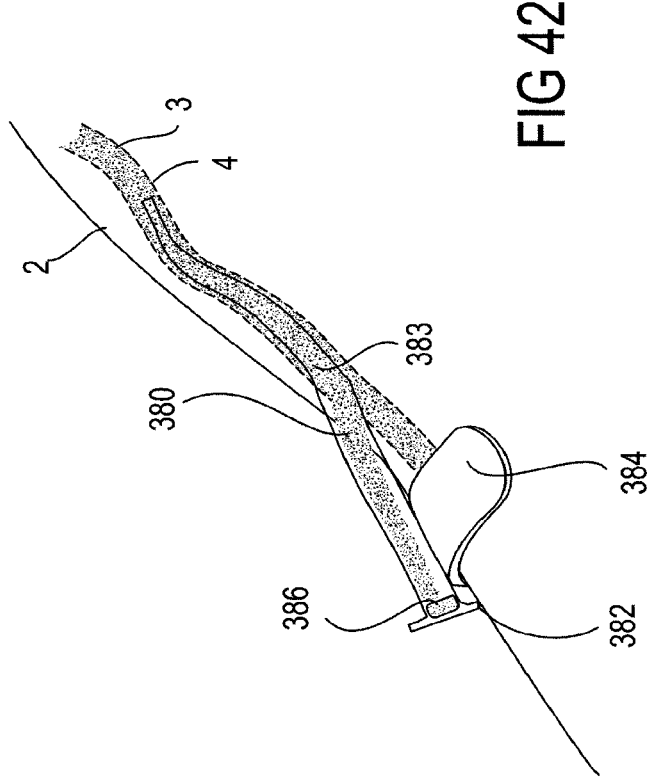

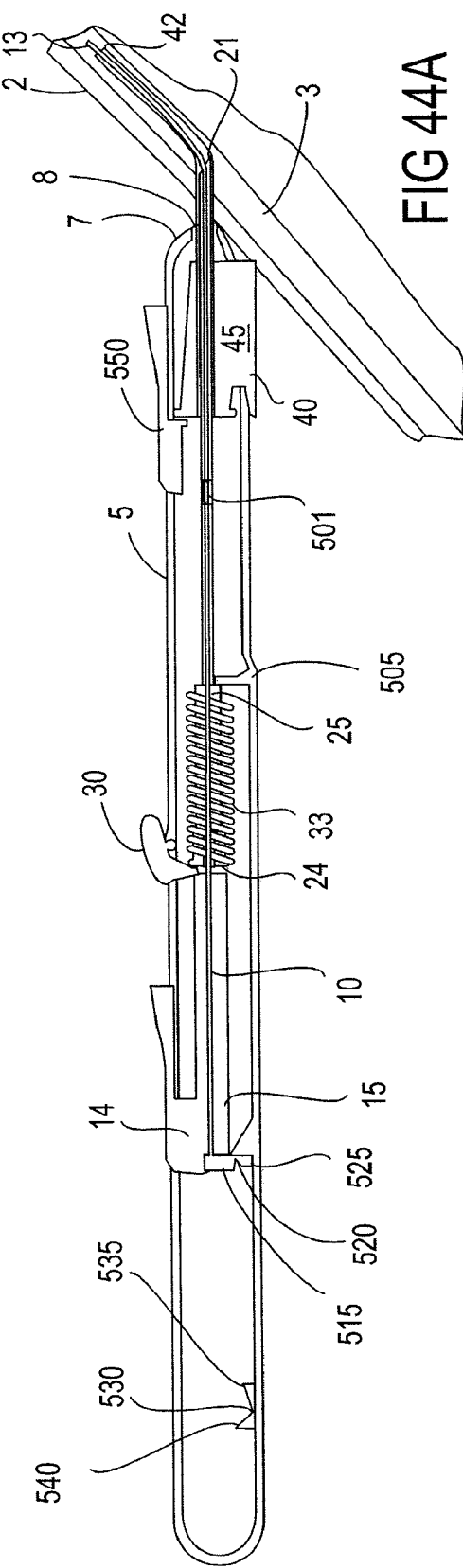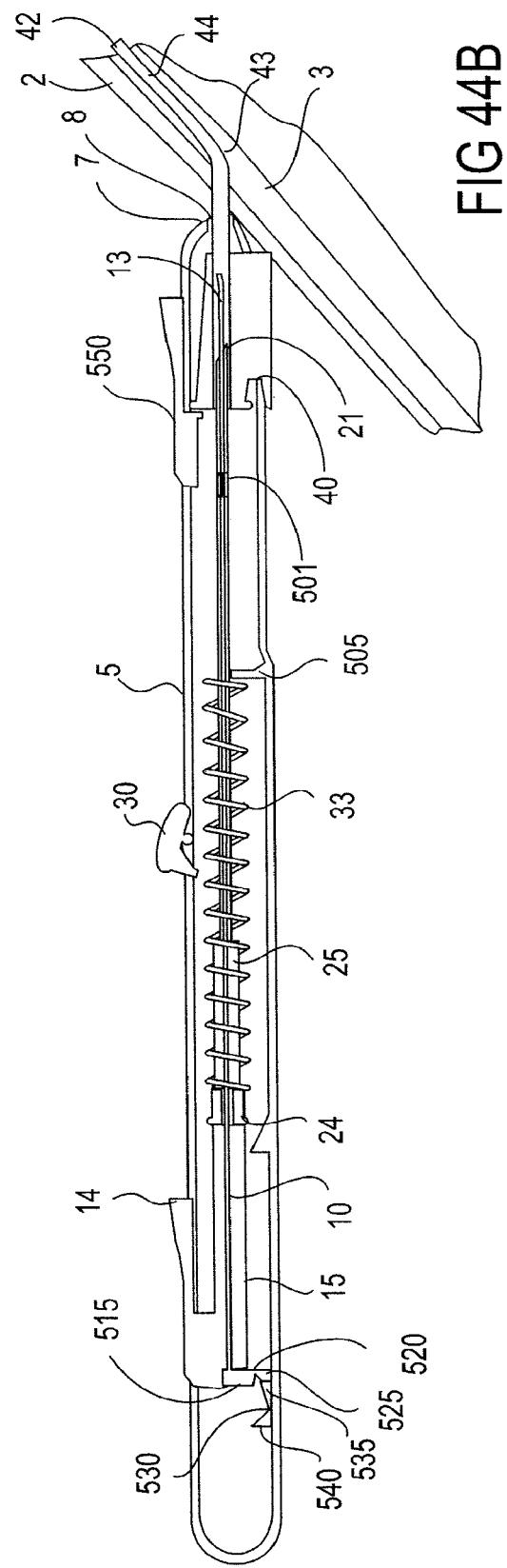

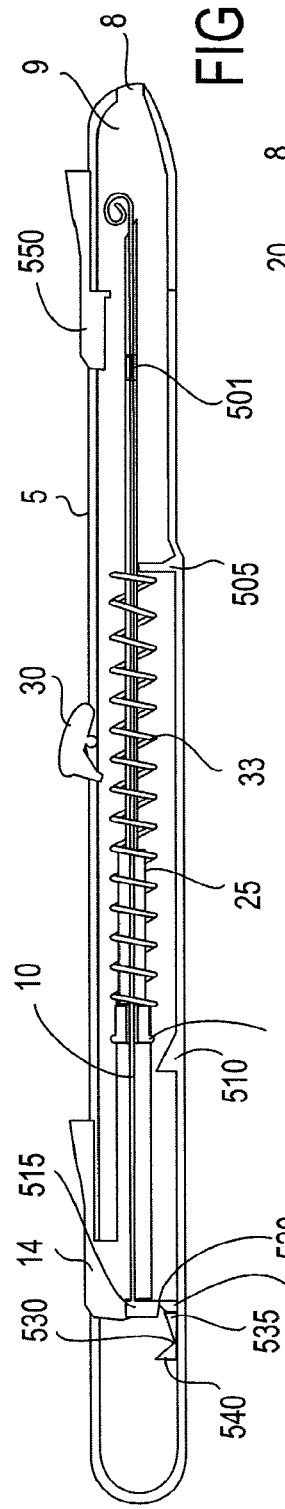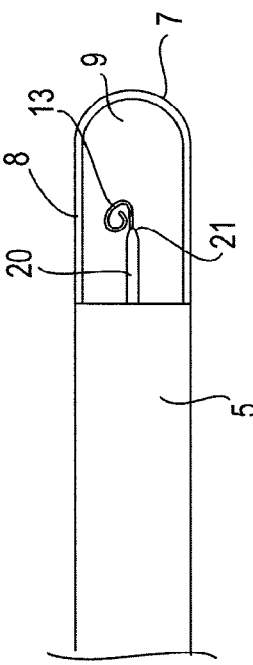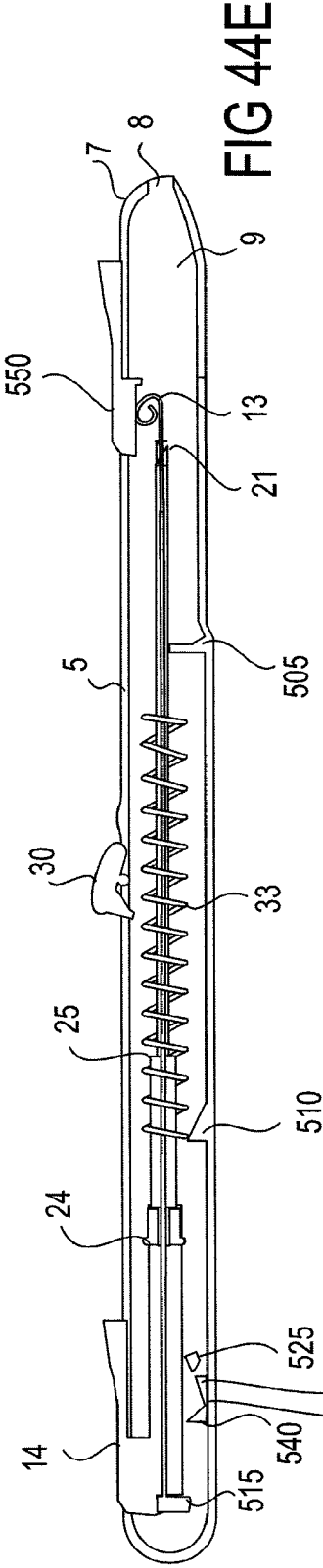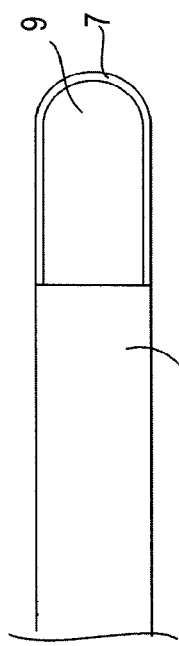

INTRAVENOUS CATHETER INSERTION AND BLOOD SAMPLE DEVICES AND METHOD OF USE

CROSS-REFERENCE TO RELATED APPLICATIONS

This application is a continuation of U.S. patent application Ser. No. 15/692,915, now U.S. Pat. No. 10,086,171, which is a continuation of U.S. patent application Ser. No. 14/876,735, filed Oct. 6, 2015, now U.S. Pat. No. 9,757,540, which is a continuation of U.S. patent application Ser. No. 14/174,071, filed Feb. 6, 2014, now U.S. Pat. No. 9,675,784, which is a continuation of U.S. patent application Ser. No. 12/598,053, filed Apr. 20, 2010, now U.S. Pat. No. 8,721,546, which is a U.S. National Stage Application of International Patent Application No. PCT/US2008/062954, filed May 7, 2008, which claims priority to U.S. Provisional Application Nos. 60/916,552 and 60/916,553, both filed May 7, 2007, the full disclosures of which are incorporated herein by reference in their entirety.

International Patent Application No. PCT/US2008/062954 is related to U.S. patent application Ser. No. 11/577,491 filed on Aug. 20, 2008, now U.S. Pat. No. 9,162,037, and International Patent Application No. PCT/US2007/068393, filed on May 7, 2007.

BACKGROUND OF THE INVENTION

1. Field of the Invention

Catheter insertion and blood collection are two activities that are often made more difficult in patients with small or collapsed vessels or with other conditions that complicate insertion of a device into the patient's vessels. In other cases, the insertion of a catheter or preparations for blood collection may be simplified in order to allow for automation of all or a part of the insertion or blood draw process. As such, a need remains for improved devices and methods for catheter placement and blood collection.

SUMMARY OF THE INVENTION

In one embodiment, there is provided method of introducing a catheter into a vessel in a patient. The method includes the steps of: inserting a needle into the vessel until a bleed back indication is provided; advancing a guide wire through the needle and into the vessel; activating a catheter advancement device; and propelling the catheter with the catheter advancement device to move along the guide wire and into the vessel. In one aspect, the activating step is performed manually by a user. In another aspect, the propelling step also includes propelling the catheter out of a housing that contains the guide wire. In alternative aspects, the bleed back indication is a visual indication such as a light. In another alternative aspect, the bleed back indication is an audible indication.

In another alternative aspect, the bleed back indication is provided as a signal produced by a bleed back sensor in communication with the needle. Alternatively, the bleed back sensor in communication with the needle is inside a housing containing a portion of the guidewire. Optionally, the signal initiates the activating a catheter advancement device step. In other aspects, the method of introducing a catheter into a vessel also includes retracting the needle and the guide wire completely into a housing after the propelling step. In other aspects, the method of introducing a catheter into a vessel also includes retracting the needle completely into a housing while retracting all but the distal end of the guide wire into the housing, after the propelling step. In other aspects, the retracting all but the distal end of the guide wire is provided by an obstruction. The obstruction may be positioned inside the housing and include a fracture able component.

In other aspects, the method of introducing a catheter into a vessel also includes stopping the propelling step when an insertion resistance detector indicates that a detected resistance to catheter advancement exceeds an allowable limit. Optionally, the method includes stopping the propelling step when a resistance to catheter advancement is greater than a force used to propel the catheter. In other alternatives, the force used to propel the catheter is a spring force, a pneumatic force, a force generated by a motor or a force generated by the movement or activation of a shape memory alloy element.

In another alternative embodiment, there is provided a method of introducing a catheter into a vessel in a patient with the steps of inserting a needle into the vessel until a bleed back indication is provided; activating a guide wire advancement device; propelling a guide wire through the needle and into the vessel; and advancing a catheter along the guide wire and into the vessel. And an additional aspect, the propelling step also includes propelling the guide wire out of a housing that contains a portion of the needle. In one aspect, the bleed back indication is a visual indication, and may be a light. In another aspect, the bleed back indication is an audible indication. In other configurations, the bleed back indication is provided as a signal produced by a bleed back sensor in communication with the needle. In one aspect, the bleed back sensor in communication with the needle is inside a housing containing a portion of the guidewire. In another aspect, the signal initiates the activating a guide wire advancement device step.

The method of introducing a catheter into a vessel may also include the step retracting the needle and the guide wire completely into a housing after the propelling step. Additionally, the method of introducing a catheter into a vessel may include the step of retracting the needle completely into a housing while retracting all but the distal end of the guide wire into the housing, after the propelling step. Additionally, the method may include the step of stopping the propelling step when an insertion resistance detector indicates that a detected resistance to guide wire advancement exceeds an allowable limit. In one aspect, the method includes the step of stopping the propelling step when a resistance to guide wire advancement is greater than a force used to propel the guide wire. An additional aspects and alternatives, the methods and devices used for device insertion or blood collection may be configured to use any combination of one or more forces to propel the guide wire and/or the catheter using a spring force, a pneumatic force, a force generated by a motor, a force generated by the movement or activation of a shape memory alloy element, or a magnetic force.

In another embodiment, there is provided an intravenous catheter insertion device. In one aspect, the intravenous catheter insertion device includes a housing having an interior space, a proximal end and a distal end defining a housing length there between. An access needle having a lumen, the access needle positioned within the interior space such that a distal end of the needle extends beyond the housing distal end. An intravenous catheter having a proximal end and a distal end, a hub on the proximal end and a lumen extending through the hub to the distal end, the intravenous catheter positioned within the housing distal end with the intravenous catheter lumen over the access needle. A guide wire within the interior space and the access needle lumen. There is also provided a catheter advancement device on the housing coupled to the catheter such that operation of the catheter advancement device moves the catheter relative to the access needle. In another aspect, the intravenous catheter insertion device includes a bleed back sensor in communication with the needle lumen. The bleed back sensor may be mounted on the housing or within the interior space. There may also be a light coupled to the bleed back sensor wherein the light illuminates when the bleed back sensor is activated. There may also be a device for emitting an audible indication coupled to the bleed back sensor wherein the device emits an audible indication when the bleed back sensor is activated. In one aspect, the bleed back sensor produces a signal that activates the catheter advancement device. In one configuration, the catheter advancement device is configured to use a force generated by a spring to move the intravenous catheter relative to the access needle. In another configuration, the catheter advancement device is configured to use a force generated by a pneumatic actuator to move the intravenous catheter relative to the access needle. In another configuration, the catheter advancement device is configured to use a force generated by a motor to move the intravenous catheter relative to the access needle. In another configuration, the catheter advancement device is configured to use a force generated by a shape memory alloy element to move the intravenous catheter relative to the access needle.

In other configurations, the intravenous catheter insertion device includes a resistance detector configured to stop the operation of the catheter advancement device when a detected resistance exceeds an allowable limit. In some configurations, the allowable limit is related to the resistance of an unobstructed catheter advancing along a guide wire. In other configurations, the allowable limit is related to the resistance of an unobstructed catheter advancing through the lumen of a blood vessel.

In one aspect, the intravenous catheter insertion device has an interior space is dimensioned to store the access needle and the guide wire after use. In one configuration the intravenous catheter insertion device, a distal end of the guide wire is visible in the housing after use. In one alternative, a view port or window is provided in the housing that permits inspection of the guide wire tip. In one configuration, operation of the catheter advancement device is initiated by a user. In other aspects, an insertion resistance detector adapted to monitor the operation of the catheter advancement device and/or a guide wire insertion device, depending upon device configuration. In one configuration of an intravenous catheter insertion device there is a notch in the housing shaped to prevent the withdrawal of the guide wire or needle into the housing. In a variation of this configuration, the intravenous catheter insertion device includes a bypass around the notch in the housing that allows the withdrawal of the guide wire or needle into the housing. In still other configurations, the intravenous catheter insertion device has a stop within the housing shaped to prevent the withdrawal of the guide wire tip into the housing and facilitate inspection of the guide wire tip.

In another embodiment, there is an intravenous catheter insertion device that includes a housing having an interior space, a proximal end and a distal end defining a housing length there between. There is also an access needle having a lumen, the access needle positioned within the interior space such that a distal end of the needle extends beyond the housing distal end. There is also an intravenous catheter that has a proximal end and a distal end, a hub on the proximal end and a lumen extending through the hub to the distal end. The intravenous catheter is positioned within the housing distal end with the intravenous catheter lumen over the access needle. There is also a guide wire within the interior space and the access needle lumen. A guide wire advancement device coupled to the guide wire such that operation of the guide wire advancement device moves the guide wire relative to the access needle lumen.

In one alternative, the intravenous catheter insertion device includes a bleed back sensor in communication with the needle lumen. The bleed back sensor may be mounted on the housing. The bleed back sensor may be within the interior space. Additionally, a light coupled to the bleed back sensor wherein the light illuminates when the bleed back sensor is activated. Additionally, a device for emitting an audible indication coupled to the bleed back sensor wherein the device emits an audible indication when the bleed back sensor is activated. In one aspect, the bleed back sensor produces a signal that activates the guide wire advancement device. In another aspect, the guide wire advancement device is configured to move the guide wire relative to the access needle lumen using a force generated by a spring, a pneumatic actuator, a motor, and/or the movement or actuation of a shape memory alloy component. Additionally, the intravenous catheter insertion device also includes a resistance detector configured to stop the operation of the guide wire advancement device when a detected resistance exceeds an allowable limit. In one alternative, the allowable limit is related to the resistance of an unobstructed guide wire advancing through the lumen of an access needle. In another alternative, the allowable limit is related to the resistance of an unobstructed guide wire advancing through the lumen of a blood vessel. In one aspect, the interior space intravenous catheter insertion device is dimensioned to store the access needle and the guide wire after use. In one aspect, the distal end of the guide wire is visible in the housing after use. In one aspect, the operation of the guide wire advancement device is initiated by a user. In another alternative, an insertion resistance detector is positioned on or in the device housing and is adapted to monitor the operation of the guide wire advancement device. Similarly, such a resistance detector may be positioned on or in the device housing and adapted to monitor the operation of the catheter advancement device.

In another embodiment, there is provided an apparatus for drawing blood. The apparatus includes a housing having a proximal end, a distal end and an interior volume. A seal is positioned within the housing partitioning the interior volume into a first interior volume portion and a second interior volume portion. A housing lumen is provided that extends from the housing distal end and is in communication with the first interior volume portion. There is a blood draw port on the housing in communication with the first interior volume portion. An access needle is provided that extends through the housing lumen. The access needle having has an access needle lumen, a distal end that extends beyond the housing distal end, and a proximal end within the second interior volume portion. There is a guidewire within the access needle lumen. In one alternative, the blood draw device includes a flexible tube positioned around the housing lumen and sized for insertion into a blood vessel. Optionally, the flexible tube is part of or is an intravenous catheter. The blood draw device may also include a nose section on the housing distal end positioned around the housing lumen.

The blood draw device may also have specific dimensions, such as, for example, a longitudinal length of the second interior volume portion is sufficient to allow movement of the access needle from a first position wherein only the access needle proximal end is within the second interior volume portion and a second position wherein both the access needle proximal portion and distal portion are within the second interior volume portion. Other dimensions include a flexible tube that is sufficiently long to maintain an overlapping region about the housing lumen while the flexible tube is inserted into a blood vessel. Additionally, the needle distal end extends beyond the distal end of the flexible tube. In another aspect, the needle distal end extends beyond the distal end of the nose section of the housing. In one embodiment, the needle distal end extends from 1 mm to 10 mm beyond the flexible tube. In still another embodiment, the needle distal end extends from 1 mm to 10 mm beyond the distal end of the nose section.

In another aspect of an insertion device, there is provided a slot in the housing and a handle within the slot coupled to the guidewire wherein movement of the handle along the slot moves the guidewire relative to the access needle lumen. Additionally, an insertion device may include a mechanism in the housing coupled to the needle and the guide wire to retract the needle and the guide wire into the second interior volume portion proximal to the seal. In another aspect, and insertion device may include a biasing element that when released withdraws one or both of the access needle and the guide wire into the second interior volume portion. In another aspect of and insertion device, when the biasing element is released, the access needle is withdrawn completely into the second interior volume portion and the guide wire distal end is visible in the first interior volume portion. In another aspect of an insertion device, when the biasing element is released the guidewire and the needle are removed from the housing lumen and the first interior volume portion. In another aspect of an insertion device, the distal end of the guidewire is curved when unconstrained by the access needle lumen.

In one aspect of a blood draw device, the blood draw port has a hollow member configured to penetrate a seal on a blood draw container. In another aspect, the blood draw port also includes a fitting having a lumen in communication with the first interior volume portion. In another aspect of the blood draw device, the flexible tube is attached to a hub.

In another aspect of the blood draw device, the seal is configured to form a seal around the guide wire when the guide wire is in the first interior volume portion and the access needle is completely within the second interior volume portion. In another aspect, the seal is configured to form a seal around the access needle while the access needle is within the first interior volume portion. In another aspect, the seal partitions the interior volume so as to substantially separate the first interior volume portion from the second interior volume portion. In another aspect, the seal partitions the interior volume but allows communication between the first interior volume portion and the second interior volume portion.

In one exemplary embodiment there is provided a method for drawing blood from a patient. The exemplary method includes the step of inserting an access needle into a vessel of the patient wherein a lumen of the access needle is in communication with an interior volume of a housing on one side of a seal within the housing that partitions the interior volume of the housing into a first interior volume portion and a second interior volume portion. Next, there is the step of advancing a guidewire though the access needle lumen and into the vessel. Next, there is the step of advancing a flexible tube along the guide wire and into the vessel. Next, there is the step of withdrawing the access needle into the second interior volume portion to place the flexible tube in communication with a blood draw port in the first interior volume portion. Finally, there is the step of withdrawing a blood sample from the vessel through the blood port.

In one aspect, the method of withdrawing blood from a patient also includes withdrawing the guidewire from the vessel and into a position where a distal end of the guide wire is visible to a user. In another aspect, the method of withdrawing blood from a patient includes withdrawing the guidewire from the vessel before, during or after the withdrawing the access needle step. In another aspect, the withdrawing the guide wire step and the withdrawing the access needle step are performed manually by a user. In still another aspect, one or both of the withdrawing the guide wire step and the withdrawing the access needle step are performed by releasing a biasing element. An alternative method, after the withdrawing the guidewire step and the withdrawing the access needle step, one or both of the access needle and the guidewire are within the second interior volume portion. In additional aspects, there is also the step of withdrawing the flexible tube from the vessel after the withdrawing a blood sample step. In other aspects, the method includes the step of disconnecting the flexible tube from the housing after the withdrawing a blood sample step while maintaining the flexible tube in the vessel. In still other aspects, the method includes the step of securing the flexible tube to the patient while maintaining the flexible tube in the vessel.

While some aspects of the invention are described in relation to the advancement or retraction of a guide wire, those aspects may also be applied to a catheter and needle. Similarly, those aspects described for catheter and needles may also be applied to guide wires and the other component as well.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In the drawings:

FIG. 9 is a section view of an intravenous catheter insertion device similar to the device of FIG. 1 with additional blood sensing and indication capabilities. FIG. 9A is a detailed view of the distal tip of the catheter of FIG. 9;

FIGS. 10 and 10A illustrate the device of FIG. 9 during needle insertion and blood detection;

FIG. 11 illustrates the device of FIG. 9 during advancement of the guide wire into a vessel;

FIG. 12 illustrates the device of FIG. 9 during advancement of a catheter out of the housing an into the vessel over the guide wire as positioned in FIG. 11;

FIG. 13 illustrates the device of FIG. 9 after automatic withdrawal of the needle and guide wire from the position in FIG. 12;

FIG. 14 illustrates an inserted catheter;

FIG. 15 is a section view of a intravenous catheter insertion device similar to the devices in FIGS. 9 and 1 with the addition of a guide wire advancement mechanism and a catheter advancement mechanism;

FIG. 16 illustrates the device of FIG. 15 during needle insertion and blood detection;

FIG. 17 illustrates the device as positioned in FIG. 16 after guide wire advancement into a vessel using the guide wire advancement device;

FIG. 18 illustrates the device as positioned in FIG. 17 after advancement of a catheter out of the housing an into the vessel using the catheter advancement device;

FIGS. 21A and 21B illustrate a pneumatically activated guide wire insertion device with a flow restrictor or flap before activation (FIG. 21A) and after activation (FIG. 21B);

FIGS. 22A and 22B illustrate a shape memory alloy (SMA) activated guide wire insertion device before activation (FIG. 22A) and after activation (FIG. 22B);

FIG. 23A shows a section view of an intravenous catheter insertion device similar to the device of FIG. 9 with blood draw capabilities and a manual catheter insertion capability;

FIG. 23B is an end view of the device of FIG. 23A;

FIGS. 24A and 24B illustrate the device of FIG. 23A during needle insertion and blood detection;

FIG. 28A illustrates an inserted blood draw device as positioned in FIG. 27 in use to draw blood samples;

FIGS. 28B and 28C illustrate section views of distally and proximally oriented seal closure designs, respectively;

FIGS. 29A-33B illustrate alternative seal designs for use in the blood draw device to partition the interior volume of the blood draw device;

FIG. 34 is a section view of an intravenous catheter insertion device similar to the device of FIG. 23A with blood draw capabilities and only capabilities for catheter and guide wire insertion and withdrawal;

FIG. 35 illustrates a section view of alternative blood sample port that may be penetrated by a sample needle;

FIG. 36 is a section view of a blood sample port connected to a flexible collection tube and an exemplary blood collection device;

FIG. 37A shows a section view of an intravenous catheter insertion device with blood draw capabilities similar to the device of FIG. 23A with outer and inner flexible tubes to provide blood draw capabilities. The device is inserted into a vessel and indicating blood detection as in FIG. 24A;

FIG. 37B is an end view of the device of FIG. 37A;

FIG. 38 illustrates the device as positioned in FIG. 37A after advancement of the guide wire into a vessel;

FIG. 42 illustrates the outer flexible tube in place and providing access to the vessel as in FIG. 41 after removal of the housing;

FIG. 43A is a view of the needle and guide wire prior to withdrawal;

FIG. 43B is an isometric view of the device in FIG. 43A after partial withdrawal of the guide wire handle to a notch that positions the guide wire tip for inspection;

FIG. 43C is an isometric view of the device of FIG. 43B after the guide wire handle has been moved to by pass the notch position shown in FIG. 43B and provide complete guide wire withdrawal into the housing;

FIGS. 44A-44F illustrate the operation of a insertion device with a manual stop to allow for guide wire inspection after use;

FIG. 44A is a section view of an insertion device after catheter advancement and prior to guide wire and needle retraction;

FIG. 44B is a section view of the device as positioned in FIG. 44A after retraction of the needle and guide wire to a first mechanical stop;

FIG. 44C is a section view of the device as positioned in FIG. 44B after separation of the catheter from the insertion device;

FIG. 44D is a bottom up view of the device in FIG. 44C with the guide wire visible in the housing;

FIG. 44E is a section view of the device as positioned in FIG. 44C after the continued withdrawal of the guide wire handle beyond the mechanical stop to a position where the guide wire and the needle are completely within the device housing;

FIG. 44F is a bottom up view of the distal end of the housing of the device as positioned in FIG. 44E showing that the guide wire is no longer within the device housing distal end.

DETAILED DESCRIPTION OF THE INVENTION

Figure 1:
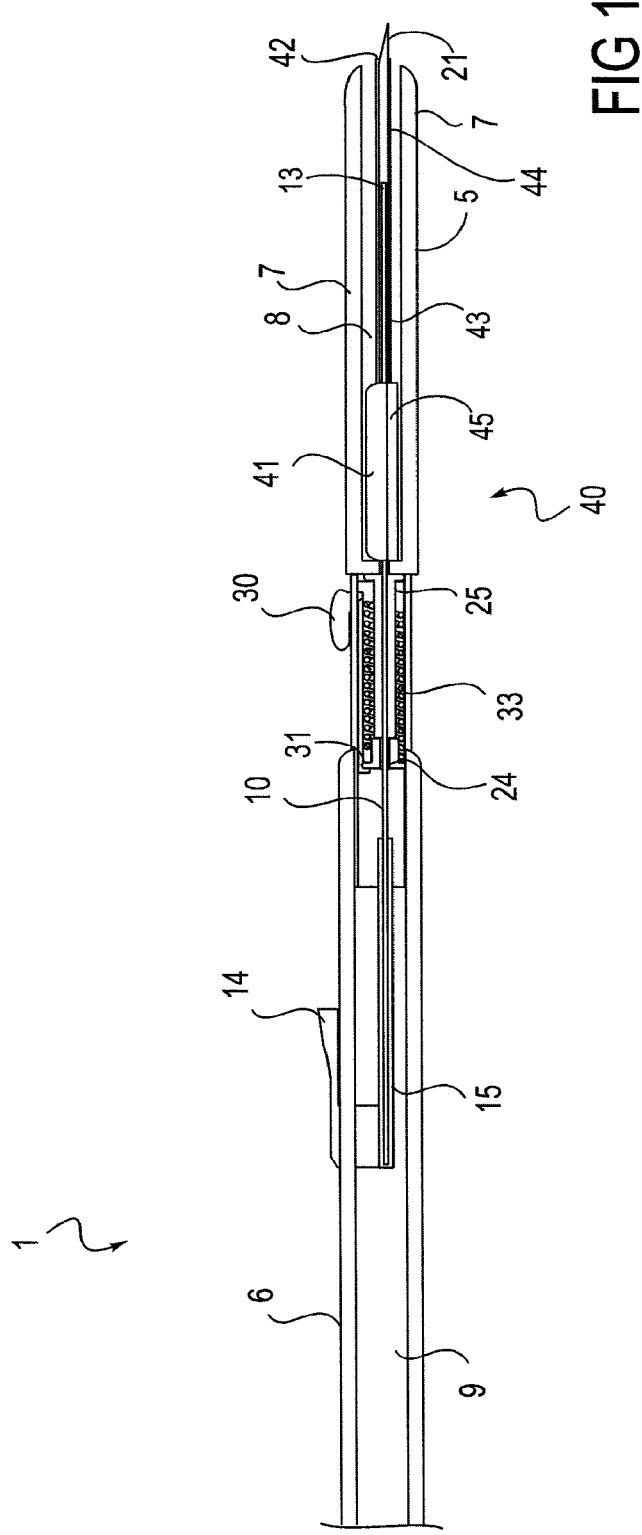
FIG. 1 is a section view of an intravenous catheter insertion device having only the distal end of the access needle extending beyond the housing distal end.

FIG. 1 shows a section view of an intravenous catheter insertion device 1 according to one embodiment the present invention. Insertion device 1 includes an insertion device housing 5 having a proximal end 6, a distal end 7 and an interior space 9. A slot 8 is provided in the distal end 7 to allow movement of the catheter hub 45 along the interior space 9. The guide wire 10 has a distal end 11, a proximal end 12 and a guide wire tip 13. The guide wire tip 13 may be straight, coiled, curved or in any of a number of shapes to allow for atraumatic insertion into and translation along a vessel. There is also a guide wire advancement lever 14 and a guide wire carrier 15. The guide wire 10 is attached to the guide wire carrier 15 and moveable relative using the guide wire advancement level 14. There is also an access needle 20 having a distal end 21, a proximal end 22 and an access needle lumen 23. The access needle 20 is contained within a needle carrier 25. The needle carrier includes a boss 24 positioned to engage with other components in the device 1 such as the release lever 31. A biasing element is shown on the needle carrier 25. The release lever 31 holds the needle carrier in place with the biasing element 33 in a compressed configuration. When the release button 30 is depressed, the release lever 31 tips up allowing the biasing element 33 to expand and move the needle carrier and the guide wire carrier in a proximal direction. The movement of the expansion element causes proximal movement of the guide wire and needle carriers that will in turn withdraw the needle and guide wire from a vessel.

FIG. 1 also illustrates a conventional intravenous catheter 40. The intravenous catheter 40 has a proximal end 41 and a distal end 42. The catheter includes a hub 45 on the proximal end attached to a flexible tube or cannula 43 that extends to the distal end 42. A lumen 44 extends from the proximal end 41 to the distal end 42 through the hub 45 and the flexible tube or cannula 43.

In the embodiment of FIG. 1, the housing 5 and interior section 8 are so dimensioned that some or the entire catheter 40 is also positioned in the housing 5. In contrast to other catheter insertion device embodiments where the catheter extends completely external to the housing distal end and the needle within it, here the catheter 40 and most of the needle 20 are stowed within the housing 5. As a result, instead of a patient seeing a full length needle extending along and through a catheter or protruding from the end of the housing, the patient only sees the tip of the needle 20 extending from the distal end of the housing 5 as shown in FIG. 1.

In some embodiments, some portion of the catheter flexible tube or cannula 43 may also be visible beyond the housing distal end 7. Operation of the device 1 is straightforward. After the needle 20 has been inserted into a vessel, the guide wire 10 is advanced into the vessel by distal movement of the guide wire knob 14. Once the guide wire 10 is extended into the vessel, the catheter 40 is advanced out of the housing 5 and into the vessel using the catheter knob (if provided as in FIG. 23A) or by simply grasping the catheter hub 45 and advancing the catheter 40 into the vessel. Thereafter, the release button 30 is used to initiate a withdrawal sequence to move both the guide wire 10 and the needle 20 to a position completely within the housing 5. The device and technique described herein could be used to place a flexible catheter into a vessel. Additionally or alternatively, once the flexible catheter is in position in the vessel, the flexible catheter is used for blood sample collection.

Figure 2:
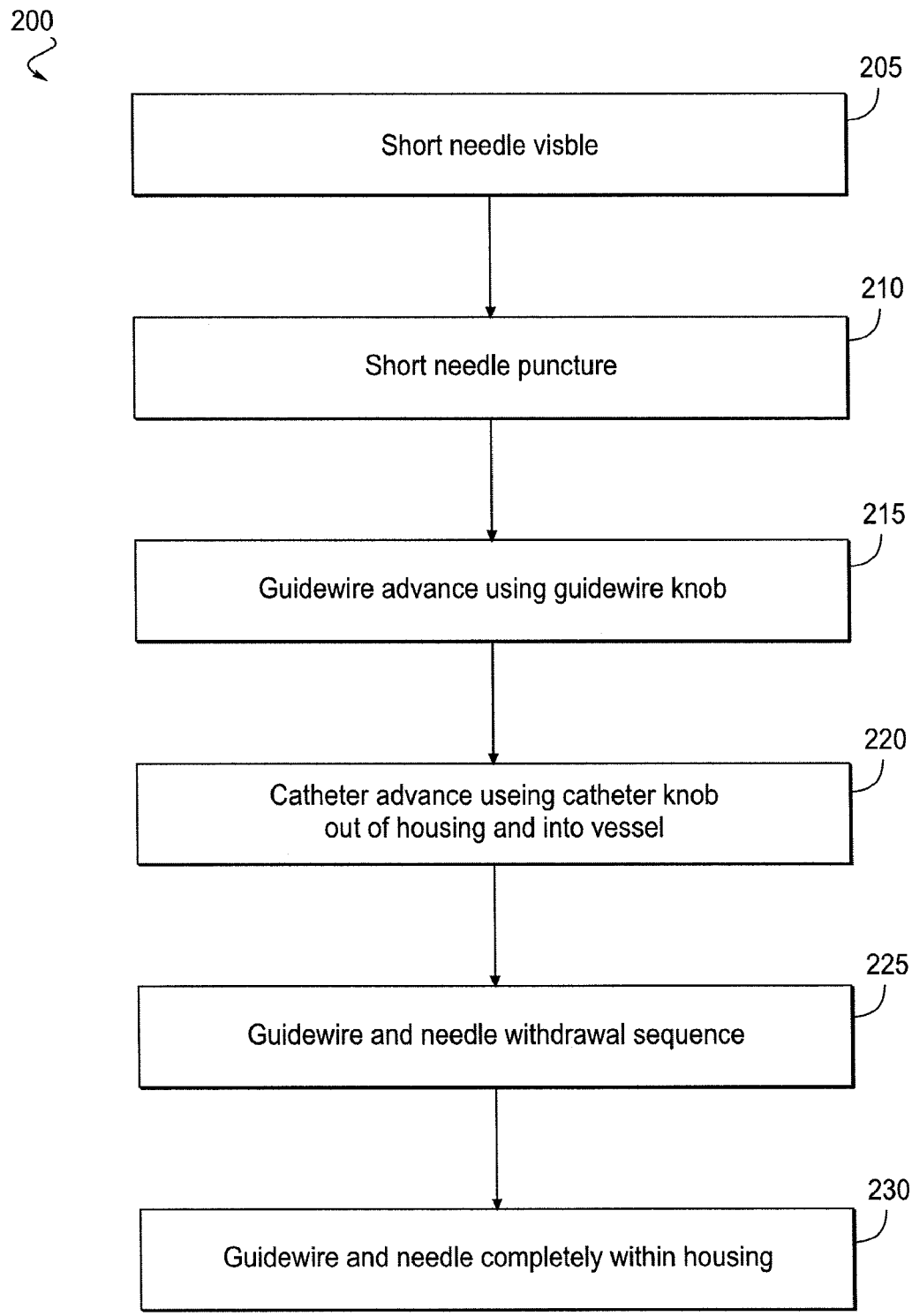
FIG. 2 is a flow chart of a catheter insertion technique using the device of FIG. 1.

FIG. 2 shows a flow chart of a catheter insertion technique using the device of FIG. 1. The device 1 is a so called short needle device because only a small amount of the needle is visible to the patient from the housing distal end. First, at step 205, the short needle is visible from the distal end of the housing. Next, step 210, the short needle is used to puncture the target vessel. The amount of the needle extending from the distal end of the housing is sufficient to perform the vessel puncture step. A conventional venipuncture needle may be used but the length of the needle is retained inside of the housing out of view from the patient. An exemplary puncture step, similar to that used by device 1, is shown in FIG. 10. Next, at step 215, the guide wire 10 is advanced through the needle 20 into the vessel. Here the guide wire advancement lever 14 is moved distally and the guide wire 10 is moved relative to the access needle lumen 23. Exemplary guide wire advancement similar to that used by device 1 is illustrated in FIG. 11.

Next, at step 220, the catheter 40 is advanced using the catheter knob (if provided) out of the housing 5 and into the vessel following along the guide wire 10. Exemplary catheter advancement, similar to that used for device 1, is shown in FIG. 12. Next, step 225, a guide wire and needle withdrawal sequence is initialed using an automatic (depress release button 30 in FIG. 1) or by manual withdrawal (see FIG. 34).

Finally, step 230, the guide wire 10 and the needle 20 are completely within the housing 5 and the catheter 40 is within a vessel. The final position of the components of device 1 after performing the method 200 are similar to that illustrated in FIGS. 13 and 14.

Figure 3:
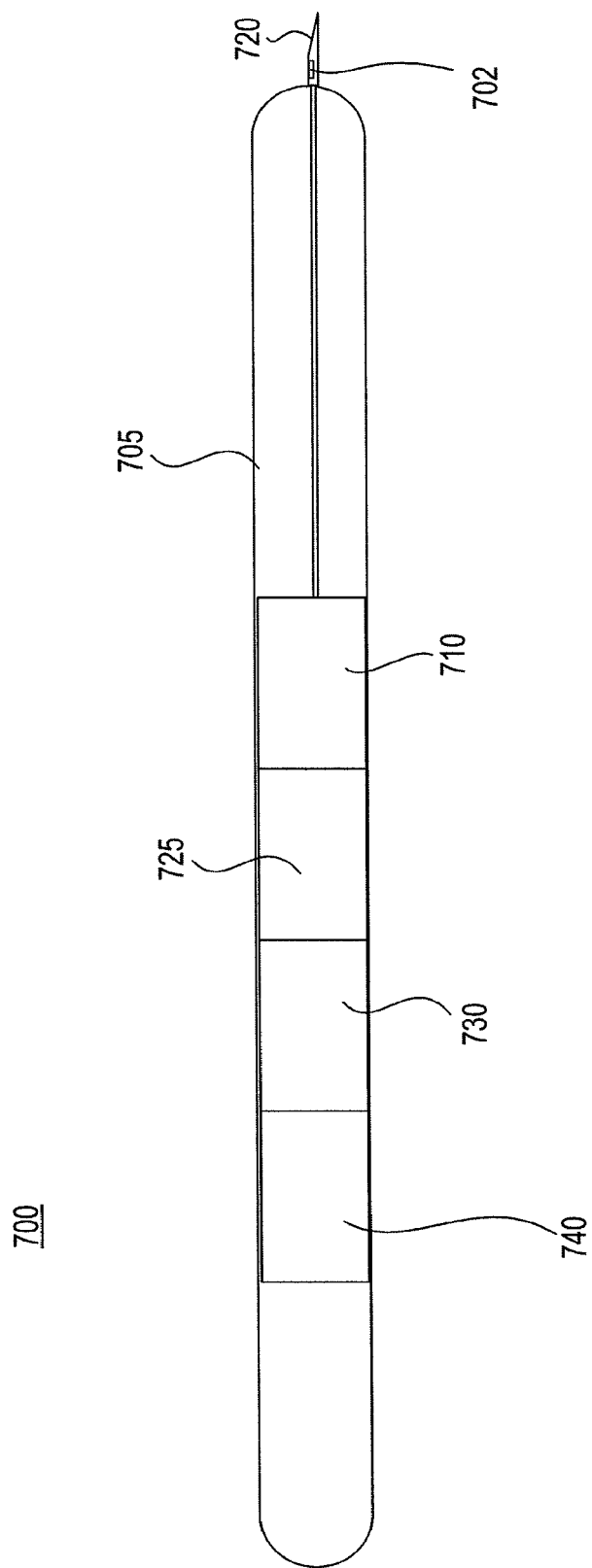
FIG. 3 is a schematic view of an intravenous catheter insertion device having one or more additional blood detection capabilities.

FIG. 3 shows a schematic view of an intravenous catheter insertion device 700 according to one embodiment the present invention. Sensors can be included in the insertion device or aspects of the insertion process can be automated as will be further described below.

The catheter insertion device 700 includes an access needle 720, a blood detection sensor 702, a housing 705, a sensing system for blood detection 710, a guidewire/needle retraction system 725, a guide wire storage area 730 and an in handle storage area 740 for storage of contaminated components. As will be understood from the embodiments that follow, many of the components illustrated in the schematic insertion device 700 may optionally be removed from an insertion device embodiment depending upon the desired functionality of the insertion device. For example, an insertion device 1 (FIG. 1) may omit the blood detection 702 and sensing system 710. The insertion device 1a may include the blood sensing capabilities omitted by insertion device 1 and so on. Additionally, a device 700 may have a retraction system 725 that is automatic as in FIG. 1 or manual as in FIG. 34.

The housing 705 contains a number of components to automate some of the steps used for catheter insertion. A needle 720 is used to access vessel. A blood detection sensor or sensors 702 are provided. The blood detection sensor 702 may be needle based as illustrated or otherwise located within the housing 705. The blood detection sensor 702 provides information to a sensing system for blood detection 710. The sensing system 710 interprets the signal produces by the blood detection sensor 702 and provides indications or triggers for other actions in the insertion process. An indication may be a signal perceptible by a user to indicate that blood is detected. A trigger may be any form of machine recognizable signaling that used by another part of the insertion device 700 to initiate a process or activate a component. Optionally, the device 700 may also include guide wire storage 730 within the housing 705 as well as adequate storage 740 for contaminated components. In many embodiments, the storage requirements for 730, 740 are sized and positioned in the housing 705 to allow for storage of the needle and guidewire used during the insertion process.

Figure 4:
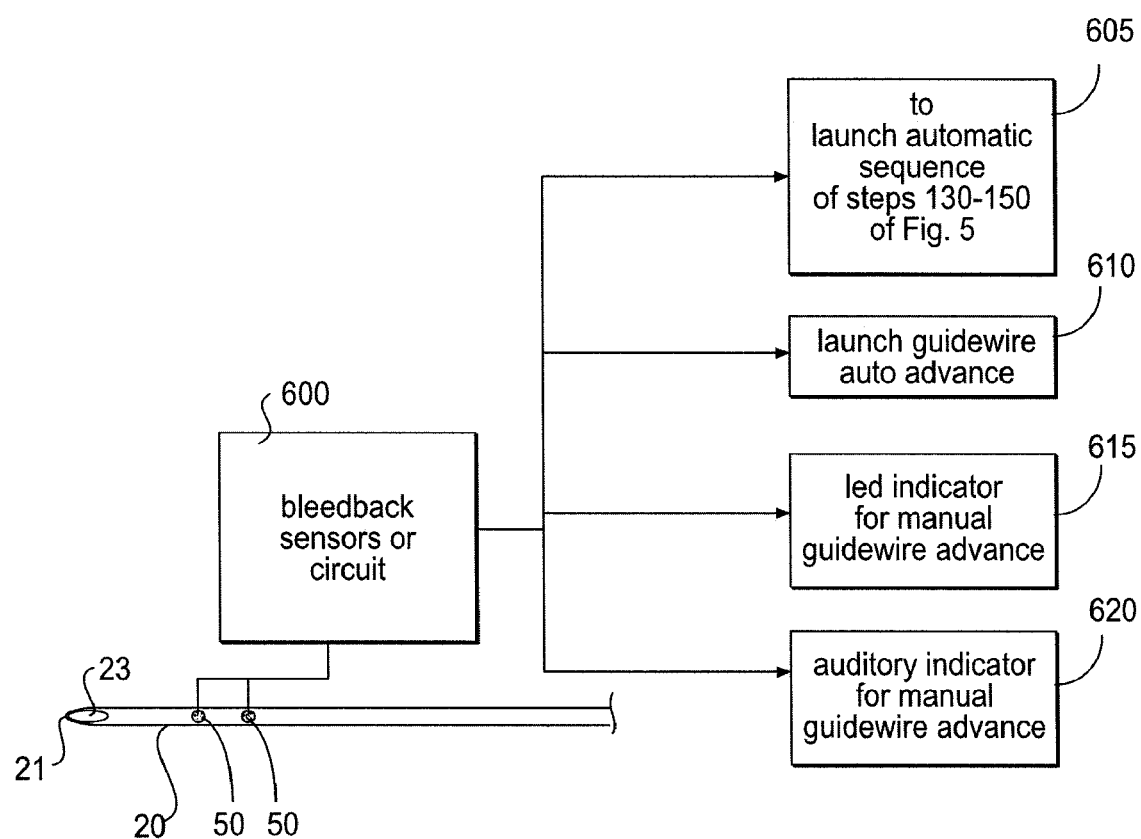
FIG. 4 illustrates schematically several event sequences for device insertion utilizing blood sensing and detection capabilities including the use of blood detection within an automated insertion device based on a detected signal.
Figure 5:
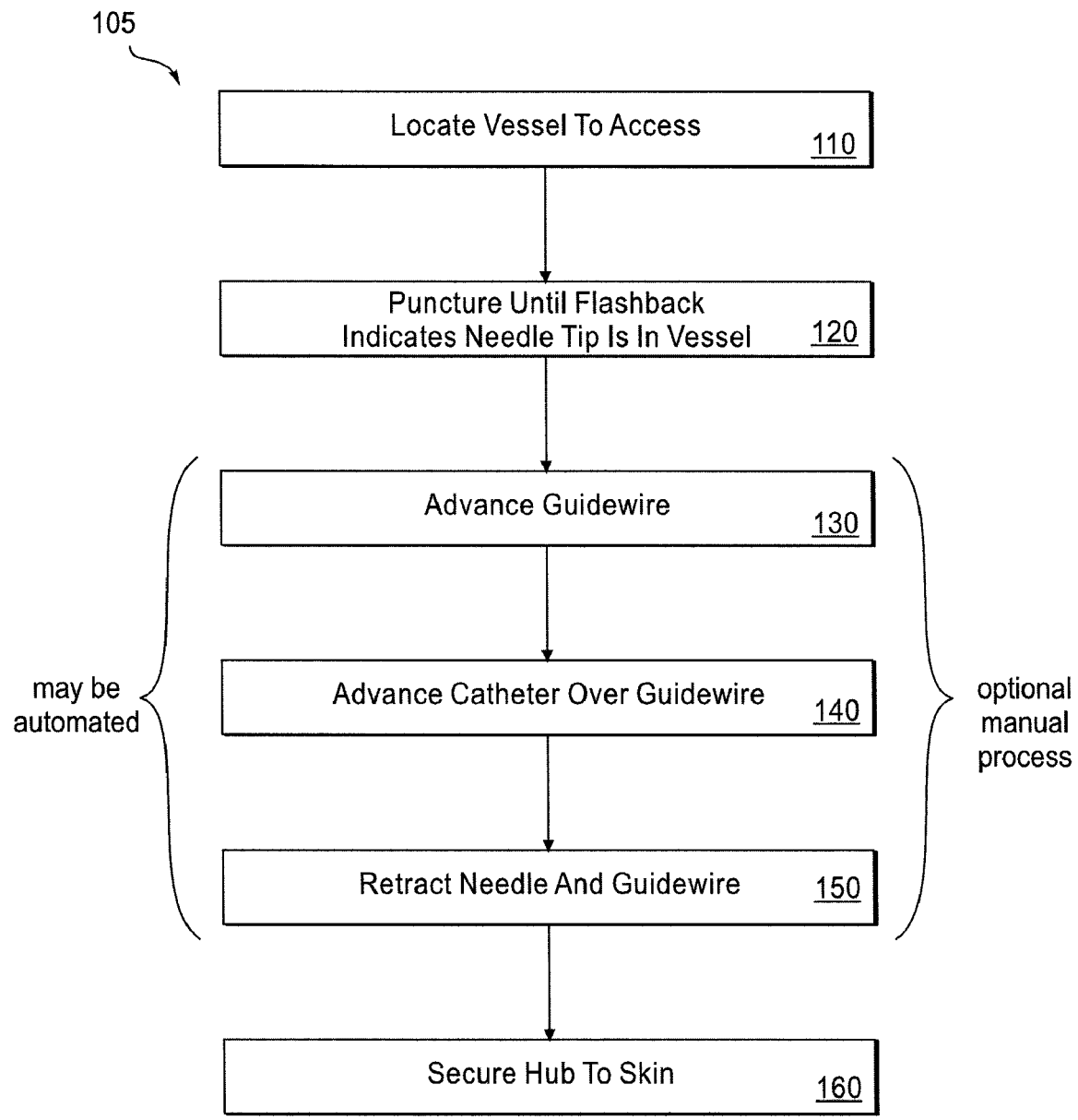
FIG. 5 is a flow chart for a catheter insertion technique using either manual or automated steps for catheter insertion device operation.

Either or both of the guide wire and access needle used in the system 700 may be adapted and configured for automatic or assisted insertion or retraction as described in the detailed examples that follow. Additionally, an intravenous catheter may optionally be configured for automatic insertion as described below. The guide wire storage 730 ensures that adequate guide wire is contained in the system for access to a wide variety of vessels including central veins. In one aspect, when the needle enters a vessel the blood detection sensors (FIGS. 6, 7, 9, 10A, 15, 24A and 37A) used in conjunction with electronic components and programming in the sensing system for blood detection may be used to provide an indication of bleed back to a user or to provide a trigger signal for some other part of the system to initiate a sequence (FIGS. 4, 5 and 8). The guide wire and/or needle retraction system includes manual and/or automatic withdrawal devices to pulling the needle and guide wire completely into the housing after use so that no sharps or blood contaminated components remain outside of the housing after use.

FIG. 4 provides an overview of possible techniques of how sensors and automation may be used. Two blood detection sensors 50 are illustrated on an access needle 20. The blood detection sensors 50 are in communication with a suitable bleed back sensor, circuit or electronic controller 600 for translating the detection signal from the sensor 50 into a signal usable by the blood detection system. While FIG. 4 provides an exemplary embodiment with two needle based blood sensors 50, other configurations are possible. For example, only one needle based sensor 50 is used. Alternatively, one bleed back sensor 50 could be used for triggering an event or action in the system (via the sensor circuit 600) and another bleed back sensor could take the form an opening that provides a visual indication of bleed back to a user. In other alternatives, the blood sensor 50 is located in a position other than in the needle 20. The bleed back sensor 50 is positioned within the housing volume or in communication with blood elsewhere on the device.

One sequence of events illustrated in FIG. 4 is the automated insertion device based on a detected signal. In this alternative, a signal from the bleed back or blood detection circuits 600 may be used in a number of ways. The signal produced by bleed back sensors/circuits 600 may be used to initiate an automatic or assisted sequence 605. The automated sequence 605 may include all or some of the steps in the method 150 (FIG. 5).

In another possible sequence, the signal from the bleed back detection circuit 600 may be used to trigger auto-advance the guide wire 610. This step may be as described in step 130 of FIG. 5 or as described below in the automatic guidewire devices that follow.

In another alternative, the bleed back signal from the bleed back circuit 600 may provide an audible (620) or visible (615) indication that manual or automatic guide wire insertion or catheter insertion may begin or resume.

FIG. 5 illustrates a method 105 having the basic steps for insertion sequence including possible automation for the process. The flow chart 105 describes a catheter insertion technique using a manual and/or automated catheter insertion techniques or devices. FIG. 5 shows a flow chart of an insertion technique 105 that may be partially or completely automated or provide assistance to a user. First, at step 110, locate the vein or vessel to access. Next, step 120, use needle to puncture the vessel until bleed back is (a) visible or (b) indicated by the system using the sensors. Next, step 130, the guide wire is advanced through the needle into the vessel. The guide wire is advanced into the vessel sufficiently far to ensure sufficient catheter guidance. Next, step 140, the catheter is advanced manually with assistance from the system or automatically using the system. Next, step 150, a guide wire and needle withdrawal sequence is initialed using an automatic or by manual withdrawal. Finally, step 230, the guide wire and the needle are completely within the housing and the catheter is secured to the patient.

In various alternative embodiments, one or more of the steps 130, 140 and 150 are adapted for automatic or assisted operation using the systems described herein.

Figure 6:
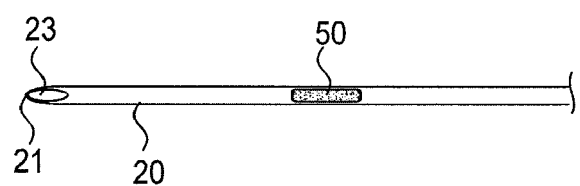
FIGS. 6 and 7 illustrate alternative positions for blood detection sensors in an access needle.
Figure 7:
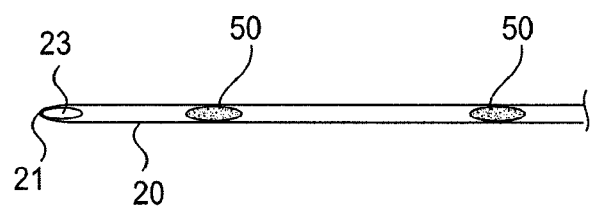
Figure 8:
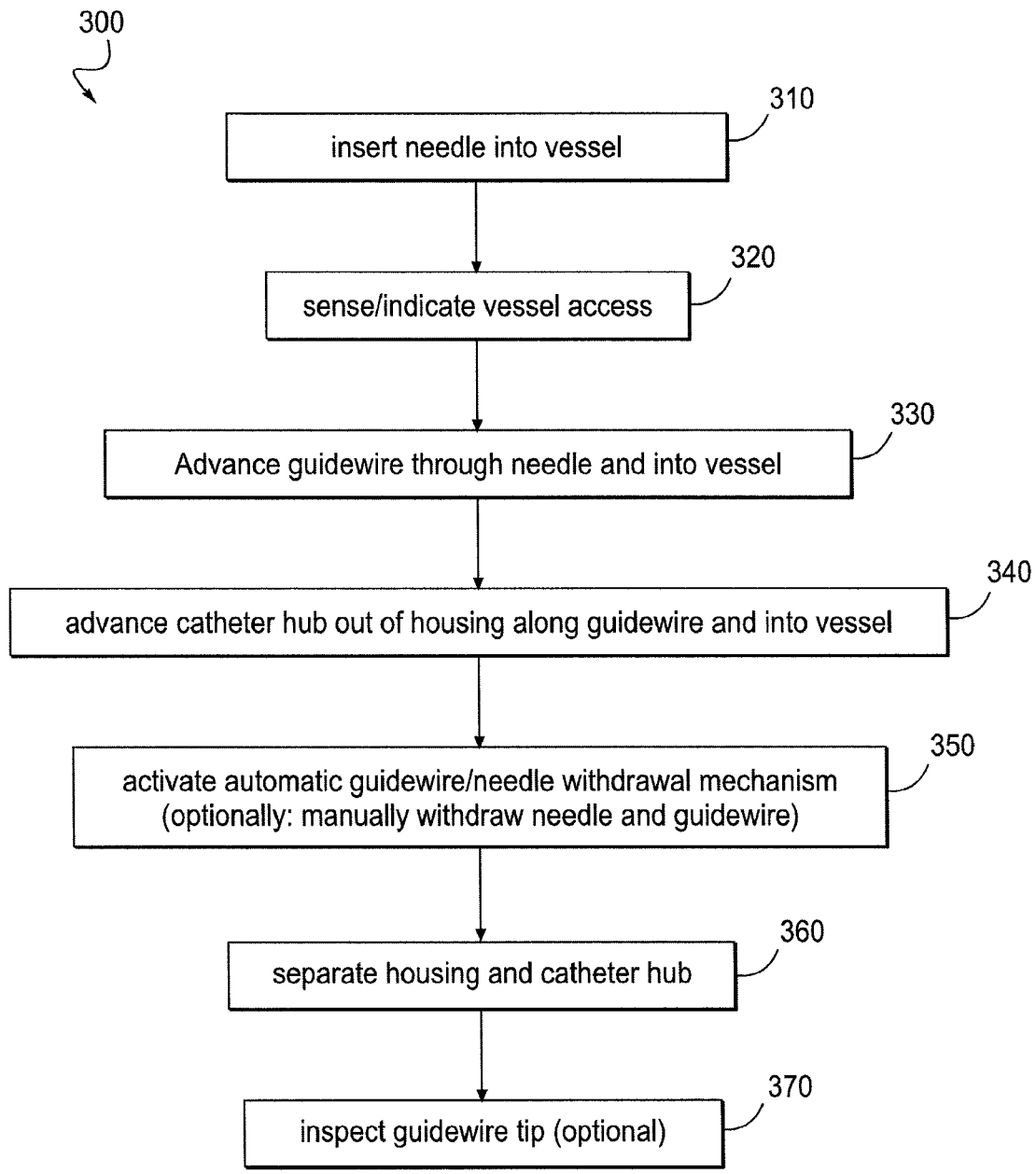
FIG. 8 is a flow chart of using a catheter insertion device having blood sensing or vessel access indication capabilities and optional automated withdrawal capabilities and optional guide wire inspection capabilities.

FIGS. 6 and 7 illustrate alternative positions for detection circuits or sensors 50 on an access needle 20. The access needle 20 has a distal end 21 and a lumen 23. The sensors may be within the lumen 23 or on the needle and in communication with the lumen 23 via a small port (not shown).

FIG. 8 is a flow chart 300 showing the steps of a catheter insertion process that incorporates one or more of bleed back sensing; automatic guidewire/needle withdrawal and guide wire tip inspection. It is to be appreciated that the steps of method 105 (FIG. 5) may also be included into the flow chart 300. In particular, some of the steps in method 300 may be automated according to the description of method 105 or other embodiments that follow that include one or both of assisted guidewire advancement and assisted catheter advancement. The insertion device 1a of FIGS. 9-14 will be discussed in relation to the exemplary insertion process set out in the steps of flow chart 300.

FIG. 9 shows a section view of an intravenous catheter insertion device 1a according to one embodiment the present invention. Device 1a is similar to the insertion device 1 with the addition of blood detection capabilities. The blood detection sensor 50 is located within the housing 5 in communication with the access needle lumen 23. A blood detection indicator 51 is in communication with the blood detection sensor 50.

FIG. 9A is an end view of the distal end 7 of the insertion device 1a. The slot 8 provides access for the catheter hub 45 to slide through the distal end 7 as the catheter hub 45 is advanced out of the device distal end and into the vessel 3 (step 340).

Similar to device 1 in FIG. 1, FIG. 9 illustrates an embodiment of a device 1a having a housing 5 and interior section 9 are so dimensioned that the catheter 40 is also positioned in the housing 5. In contrast to other embodiments where the catheter extends completely external to the housing distal end and the needle within it, the catheter and most all of the needle are stowed within the housing. As best seen in FIGS. 9 and 10, the needle distal end 21 extends just beyond the housing distal end 7. As a result, instead of a patient seeing almost an entire needle extending along and through a catheter hub, the patient only sees the tip of the needle extending from the distal end 7 of the housing 5. In some embodiments, some portion of the catheter lumen (such as the distal end 42) may also be visible beyond the housing distal end 7 (see FIG. 9). Alternatively, the catheter distal end 42 may be proximal to the housing distal end 7 as shown in FIG. 10. After the needle 20 has been inserted, the guide wire 10 is advanced by moving the guide wire knob 14. Once the guide wire 10 is extended into the vessel 3, the catheter 40 is advanced out of the housing 5 and into the vessel 3 using, for example, a re-useable catheter advancement device described below.

As described below in the embodiment of FIG. 15, a catheter advancement motor or drive may be used to propel the catheter out of the housing to propel a length of catheter lumen or other flexible medical grade line from storage along the guide wire and into a vessel. In some embodiments, an insertion resistance detector monitors the catheter advancement device and/or the flexible tubing for indications that resistance in the vessel is outside of allowable limits for catheter advancement. One instance when resistance may exceed limits is if the catheter is advanced into a vessel wall or other obstruction. If insertion resistance is detected, then the system may stop the advancement device and/or provide an alarm to the user.

Once the automated catheter insertion sequence is completed, the release button 30 is used to initiate a withdrawal sequence to move both the guide wire 10 and the needle 20 completely within the housing. Optionally, the useable catheter insertion device may them be sterilized as needed and another catheter loaded into the catheter advancement housing. Then, the catheter advancement housing is loaded onto the distal end of the housing and the needle inserted into the catheter into the position illustrated in FIG. 9. The device is ready for another insertion sequence.

Returning now to the method of FIG. 8 and the device 1a in FIG. 9. First, according to step 310, insert a needle into a vessel. FIG. 10 illustrates the movement of the components of the embodiment of FIG. 9 as an example of how this step of the method may be accomplished.

Next according to step 320, sense/indicate vessel access. This step is includes the detection of bleed back and may include some or all of the aspects described above in relation to FIG. 4. FIG. 10A is a close up of the view illustrated in FIG. 10. FIG. 10A illustrates a sensor 50 in communication with the access needle lumen 23. Blood 4 has advanced up the needle lumen 23 into contact with the sensor 50. As a result, the indicator 51 is triggered to show that bleed back is present. In the illustrated embodiment, the indicator is a light or light emitting diode (LED).

Bleed back is a common indication of the needle tip entering the target vessel and blood coming into the needle and becoming visible to the user. While the user may also perceive the bleed back indication, embodiments of the present invention also can be used to detect, indicate or trigger actions based on bleed back. It is to be appreciated that any of a wide variety of signals and detection techniques can be used to determine whether blood has entered the needle. These range from the visual indication of blood in the needle or housing. The detection of blood may also be provided by a blood detecting sensor. Additionally, the detection of blood could be performed by any type of signaling or detection technique to identify the passage of blood though the needle or to indicate that the needle has entered a vessel. These include detection techniques based on light, optics, pressure or sound. The components of the electronics and sensors 600 (FIG. 4) are modified as needed to detect and determine bleed back based on the type of sensor used. FIG. 10A illustrates the movement of the components of the embodiment of FIG. 9 as an example of how this step of the method may be accomplished.

Next according to step 330, advance a guide wire through a needle and into a vessel. FIG. 11 illustrates the movement of the components of the embodiment of FIG. 9 as an example of how this step of the method may be accomplished. Here, the guide wire advancement lever 14 has been moved distally. This movement advances the guide wire 10 through the access needle lumen 23 and into the vessel 3. The guide wire tip 13 is rounded to allow for atraumatic advancement of the guide wire through and along the vessel 3.

Next according to step 340, advance a catheter 40 out of the housing 5 along the guide wire 10 and into the vessel 3. FIG. 12 illustrates the movement of the components of the embodiment of FIG. 9 as an example of how this step of the method may be accomplished. Here, a user may grasp the catheter hub 45 and, while holding the device stationary, advance the catheter 40 out of the housing 5 and into the vessel as shown. Note how the slot 8 is sized to allow access to and passage of the catheter hub 45.

Next according to step 350, activate an automatic guide wire and/or needle withdrawal mechanism. FIG. 13 illustrates the movement of the components of the embodiment of FIG. 9 as an example of how this step of the method may be accomplished. Once the release button 30 is pressed, the biasing element 33 moves the guide wire and needle proximally as shown in FIG. 13. Note that the guide wire tip 13 is available for inspection through the housing distal end 7 (if the housing is transparent) or in any event by viewing the guide wire tip 13 though the slot 8.

FIG. 13 illustrates the automatic withdrawal of the needle and guide wire. Optionally, the needle and guide wire may be manually withdrawn from the vessel and into the device housing. The device in FIG. 34 is an example of an insertion device configured for manual withdrawal.

Next according to step 360, separate the housing 6 and the catheter 40. FIG. 14 illustrates the result of separation of the catheter 40 and the device body 5. FIG. 14 shows the tip of the catheter 42 in the vessel 3 and the catheter hub 45 on the patient's skin 2. The device housing appears as in FIG. 13 with the change that the catheter 40 is removed from the housing distal end 7.

Next according to step 370, inspect the guide wire tip 13. The guide wire tip 13 is visible in the distal end of the housing 7. This allows the guide wire tip 13 to be inspected as described in step 370. FIG. 13 illustrates one embodiment of a catheter insertion device that provides for guide wire tip 13 inspection, if such inspection is required or recommended.

Some regulatory authorities may require inspection of the guide wire 10 after use in the body. The embodiments of FIGS. 13, 19, 23A, 28A, 37A, and 40 each provide for inspection of the guide wire 10 after use in the body. Additionally, the housing and other components that are near or envelope the guidewire 10 may be made from clear medical grade or other suitable plastics. In this way, the catheter insertion device may operate normally but because the components around the guide wire are clear, the guide wire inspection may precede unimpeded. Other guidewire tip inspection devices are described below, for example, in FIGS. 43A-44F.

Returning briefly to the method described in flow chart 105 of FIG. 5. The steps of advancing and retracting the guide wire and the needle may be automated. FIG. 15 illustrates an embodiment of a catheter insertion device where all the steps 130, 140 and 150 are provided for automation. While the embodiment of FIG. 15 illustrates the automation of all of these steps, other embodiments of the catheter insertion device of the invention may include automation of one or more of the steps 130, 140 and/or 150. For example, the catheter insertion device in FIG. 1 illustrates a spring retraction device to automate the needle and guidewire (step 150) but provides for only manual insertion of the guidewire and catheter (steps 130 and 140). The various steps may be automated or performed manually as the situation and design dictate. One of ordinary skill will appreciate that the various alternative manual and automated embodiments may be recombined in any number of different configurations within the scope of the present invention.

FIG. 15 is a section view of FIG. 15 is an insertion device 1*b* that is similar to insertion device 1*a* with the addition of both a guide wire advancement mechanism 55 and a catheter advancement mechanism 60. While both are illustrated in this exemplary embodiment, it is to be appreciated that either advancement mechanism or no advancement mechanism may be used in an insertion device. The guide wire advancement mechanism 55 includes a hinge 56, a motor 57 and rollers 58. The catheter advancement mechanism 60 includes a hinge 61, a motor 62 and rollers 63. The insertion device 1*b* also includes a blood sensor 50 and an indicator 51. Here, the sensor 50 and or the indicator 51 may be used to trigger operation of the guide wire 55 or catheter 60 insertion devices. Additionally, signaling from the guide wire insertion device may be used to trigger the operation of the catheter insertion device. A trigger such as range of motion indicating that the guide wire is completely inserted or a motion detector or other trip, such as a reed switch, to indicate that guide wire motion is complete or hindered may also be an input to the catheter advancement device.

One method for inserting a catheter 40 using insertion device 1*b* will be described with reference to FIGS. 16-19. The insertion technique is similar to that described above with reference to FIGS. 10-14.

FIG. 16 illustrates the needle 20 puncturing the vessel 3. The sensor 50 will detect the presence of blood 4 and the indicator 51 will inform the user of the presence of blood 4 in the needle lumen 23. Once the indicator 51 is activated, the user is informed of the successful vessel puncture.

FIG. 17 illustrates an automated version of step 130 in method 105 (FIG. 5). Here, the sensor 50 is used to also activate the operation of the guide wire advancement motor 57. Operation of the guide wire advancement motor 57 causes rotation of the rollers 58. Rotation of the rollers 58 causes the guide wire 10 to move from within the needle lumen 23 and into the vessel 3. The final position of the guidewire 10 and guide wire tip 13 after operation of the guide wire advancement motor 57 is shown in FIG. 17.

The guide wire advance motor 57 may cease operation by any of a number of conventional techniques for monitoring the operation of a motor or movement of an object. An encoder may be used to count the number of rotations of the motor 57, the rollers 58, a lead switch may interrupt operation of the motor once the guide wire carrier has moved beyond a certain point, or an obstruction may be positioned within the housing that, when contacted by the guide wire or the guide wire carrier causes the guide wire advancement motor to cease operation.

Additionally, any of a number of strain or resistance gauges could be coupled to the guide wire, a guide wire component, the catheter, a catheter component or into a position on or in the housing in order to provide an indication of when the guide wire and/or catheter has struck an obstruction or otherwise ceased unobstructed movement through the vessel 3. These are merely exemplary of any of a wide variety of conventional sensing and detection means that may be coupled to the guide wire or the catheter or their carriers to assist in determining movement, range of movement or unobstructed movement. The output of the resistance sensing or detection means may be used as in input to the insertion control system used to control the operation of the guide wire advancement device or the catheter advancement device or even to monitor insertion controlled by a user to ensure the user receives feedback that the advancement is not unobstructed or that resistance to insertion in increasing.

In other aspects, the method of introducing a catheter a guide wire into a vessel also include the step of stopping the propelling step when an insertion resistance detector indicates that a detected resistance to catheter advancement exceeds an allowable limit. Optionally, these methods may include stopping the propelling step when a resistance to catheter or guide wire advancement is greater than a force used to propel the catheter or guide wire. This refers to the low force or low speed alternatives described below that use pneumatic, low force springs, shape memory alloy activated components or other suitable low force/low power advancement alternatives such as the motors selected for the guide wire and catheter advancement devices. In other alternatives, the force used to propel the catheter or the guide wire is a spring force, a pneumatic force, a force generated by a motor or a force generated by the movement or activation of a shape memory alloy element.

In another alternative, an insertion resistance detector is positioned on or in the device housing and is adapted to monitor the operation of the guide wire advancement device. Similarly, such a resistance detector may be positioned on or in the device housing and adapted to monitor the operation of the catheter advancement device.

FIG. 18 illustrates an automated version of step 140 in method 105 (FIG. 5). Here, the sensor 50 may also used to also activate the operation of the catheter hub advancement motor 62. Alternatively, the catheter advancement mechanism may be separately actuated by a user or as a result of a trigger provided by a control system of received from the guide wire advancement mechanism or a system controlling the guide wire advancement. Operation of the catheter hub advancement motor 62 causes rotation of the rollers 63. Rotation of the rollers 63 causes the catheter 50 to move from within the distal end of housing 7 and into the vessel 3. The final position of the catheter 40 after operation of the catheter hub advancement motor 62 is shown in FIG. 18. Note how the hinge 61 allows deflection of the catheter advance mechanism 60 to deflect in response to contact with the catheter hub 45. This deflection may be a trigger to cease operation of the motor 62.

The catheter advance motor 62 may cease operation by any of a number of conventional techniques for monitoring the operation of a motor or movement of an object. An encoder may be used to count the number of rotations of the motor or the rollers 63, a lead switch may interrupt operation of the motor once the catheter 40 has moved beyond a certain point, or an obstruction may be positioned within the housing that, when contacted by the catheter causes the catheter advancement motor 62 to cease operation. Deflection of the hinge 56, 61 may be used as a signal to cease operation of a motor or other advancement device.

Additionally, any of a number of strain or resistance gauges could be coupled to the catheter to provide an indication of when the catheter has struck an obstruction or otherwise ceased unobstructed movement through the vessel 3. These are merely exemplary conventional sensing and detection means that may be coupled to the catheter to assist in determining catheter movement or range of movement. The output of the sensing or detection means may be used as in input to the insertion control system used to control the operation of the catheter advancement device.

Figure 19:
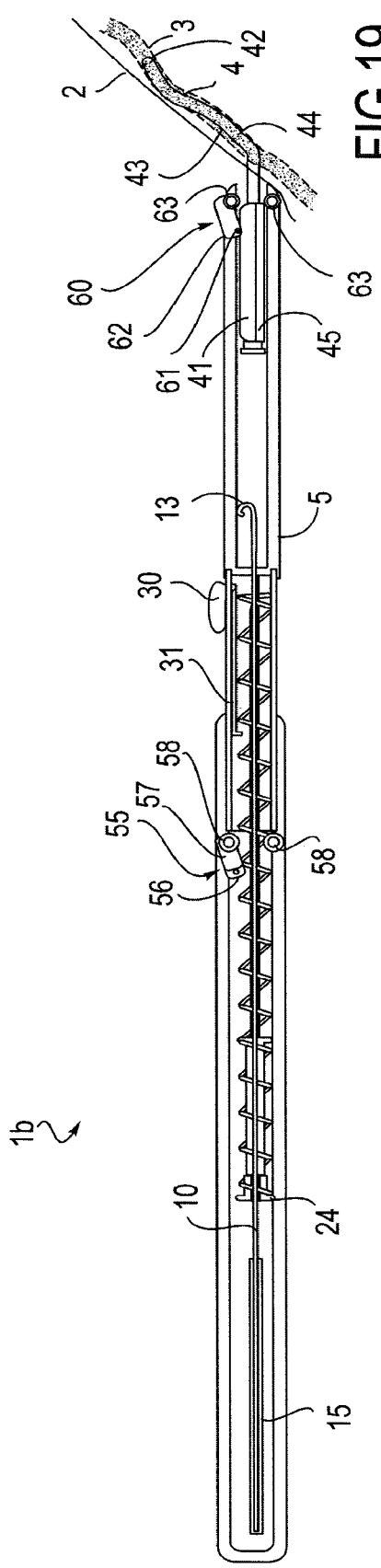
FIG. 19 illustrates the device as positioned in FIG. 18 after automatic withdrawal of the needle and guide wire from the vessel and catheter.

FIG. 19 illustrates a version of step 150 in method 105 (FIG. 5). Here, the user moves the release 30 to also allow the spring or other biasing element 33 to withdraw the needle 20 and the guide wire 10 out of the vessel 3 and catheter 40. As shown in FIG. 19 the guide tip 13 is also visible in the distal end 7 or via slot 8 to allow for easy inspection, if needed. Thereafter, the catheter 40 is removed from housing 5 and secured to the patient as shown in FIG. 14 and in accordance with step 160 (FIG. 5).

Automated advancement and withdrawal of components may be accomplished using any suitable technique such as the motors, springs or biasing members described herein. Additionally, pneumatic systems may be used to advance, withdraw or otherwise move components of the catheter delivery systems described herein. For purposes of illustration, the following examples are described with regard to one component. It is to be appreciated that these alternative actuation techniques may be applied to the assisted or automated movement of any component in the device.

Figure 20A:
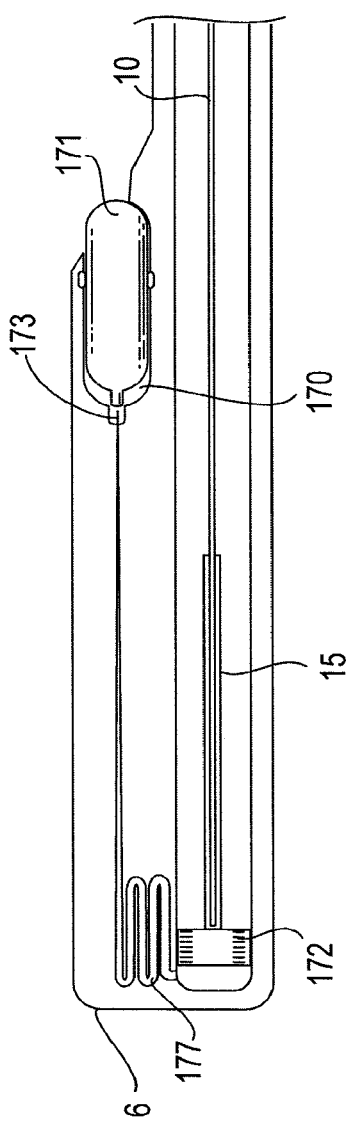
FIGS. 20A and 20B illustrate a pneumatically activated guide wire insertion device before activation (FIG. 20A) and after activation (FIG. 20B)
Figure 20B:
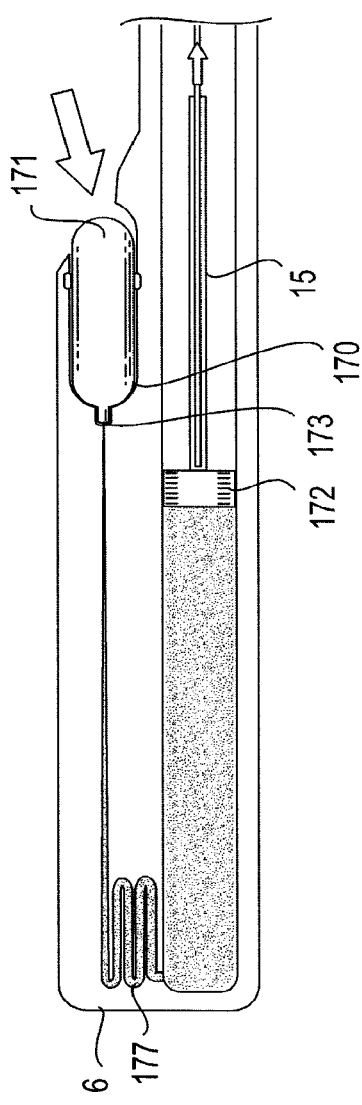

FIGS. 20A and 20B illustrate a catheter advancement device having a pneumatically actuated guide wire advancement component. As shown in FIGS. 20A and 20B the housing proximal end 6 modified to include a recess 170 shaped to receive the pneumatic source 171. The pneumatic source 171 could be any conventional container of compressed gas. The recess in shaped to provide a friction fit for the pneumatic source 171 into the housing 5. The pneumatic pathway 177 provides communication between the recess 170 and the plunger 172. The pneumatic pathway may take on any of a variety of shapes and dimensions to allow the release of compressed gas in the source 171 to move the plunger 172 to provide a low force or controlled movement of the guide wire 10. The guide wire carrier 15 has been modified to include a plunger 172. The housing is sized to provide a fluid tight fit between the plunger 172 and the interior of the housing.

FIG. 20B illustrates the pneumatic source in use to move the plunger 172. When the pneumatic source 171 is moved as indicated by the arrow and into contact with the puncture tip 173, the contents of the source 171 are released into the pneumatic pathway 177 and push the plunger 172. Movement of the plunger 172 moves the guide wire in the direction of the arrow (into a vessel).

FIGS. 21A and 21B illustrate a catheter advancement device having another pneumatically actuated guide wire advancement component.

Similar to FIGS. 20A and 20B, the pneumatic source 171 is used to provide controlled, low force movement of the plunger 172 that in turn moves the guide wire into a vessel. As shown in FIGS. 21A and 21B the housing proximal end 6 modified to include a recess 170 shaped to receive the pneumatic source 171. In contrast to the embodiment above, the pneumatic pathway 172 includes a flap or restrictor 174 to further control the release of the contents of the pneumatic source 171 through the pneumatic pathway 171. As shown here, the pneumatic pathway may take on any of a variety of shapes and dimensions to allow the release of compressed gas in the source 171 to move interact with the restrictor 174 and move the plunger 172 to provide a low force or controlled movement of the guide wire 10.

FIG. 21B illustrates the pneumatic source in use to move the plunger 172. When the pneumatic source 172 is moved as indicated by the arrow and into contact with the puncture tip 173, the contents of the source 171 are released into the pneumatic pathway 172, past the restrictor 174 and push the plunger 172. Movement of the plunger 172 moves the guide wire in the direction of the arrow (into a vessel).

FIGS. 22A and 22B illustrate a catheter advancement device having a guide wire advancement component that utilizes shape memory alloy (SMA) element or elements to facilitate guidewire movement. Housing proximal end 6 modified to include a shape memory alloy guide wire 10a and the proximal end 12 attached within the housing proximal end 6. The wire 10a is attached to the guide wire carrier 15 (not shown).

For clarity, a conventional shape memory alloy power supply and controller are not shown. The components may be on, in or separate from the insertion device housing. A conventional power source is attached to the SMA guide wire. Once activated, the SMA guide wire 10a is used to advance the guidewire carrier 15 along the housing and to push the guide wire tip 13 into a vessel (movement indicated by the arrow in FIG. 22B). It is to be appreciated that the SMA activation properties can be controlled to minimize the speed or otherwise provide a low force advancement of the guide wire. Additionally, circuitry and suitable electrical connections may be provided to the SMA controller that will cut power to the SMA guide wire 10a in the event that friction or an obstruction is encountered that may indicate that the guide wire is not advancing normally though the vessel.

While the pneumatic and shape memory alloy devices have been described for the movement of a guidewire, the invention is not so limited. These alternative advancement techniques may also be used for the advancement of a catheter or other moveable component as described herein. For example, the SMA element in FIGS. 22A and 22B may be replaces by a low force spring to advance the guide wire or otherwise configured to advance the catheter. A low force spring in this context as well as the low force of the other advancement modes is a force that is low enough to provide the desired movement of the catheter or guide wire. However, as a safety precaution, the force generated is low enough that if it encounters increasing resistance (for example if the component hits an obstruction in a vessel or is misdirected into a vessel wall) then the device movement will cease. In some aspects, when such resistance is encountered or detected, an alarm or other indication of resistance, similar to those used for blood detection, may be provided to the user or the control system.

FIG. 23A illustrates an insertion device 1c adapted to provide blood draw capabilities. The blood draw device 1c is similar to the device 1b of FIG. 9. Unlike the embodiment illustrated in FIG. 9, the embodiment of FIG. 23A includes several components and reconfiguration of existing components to provide blood draw capabilities. Additionally, the portion of the housing 5 in the vicinity of the blood draw port 180 has been modified to accommodate the additional requirements of drawing blood.

Because the blood draw device includes blood sensing capabilities, the operation and use of the blood draw device 1c is similar to the steps described above with regard to FIGS. 10-13.

FIG. 23A is a section view of an apparatus for drawing blood. The blood draw apparatus 1c has many components in common with previously described insertion devices 1, 1a and 1b. The blood draw apparatus 1c includes a housing 5 having a proximal end 6, a distal end 7 and an interior volume 9. A seal 186 within the housing 5 partitions the interior volume 9 into a first interior volume portion 9a and a second interior volume portion 9b. A housing lumen 9c extends from the housing distal end 7 and is in communication with the first interior volume portion 9a. The apparatus 1c also includes a view port 185 for inspection of the guide wire tip 13. The housing distal end 7 has a nose section 7a. The nose section 7a has a lumen and interior volume configured to fit over the flexible tube 195.

There is also provided a blood draw port 180 on the housing 5 in communication with the first interior volume portion 9*a*. The blood draw port 180 includes a fixture 181 to receive a blood draw container 182. A seal 183 may also be provided in the blood draw port or to maintain a fluid tight seal with blood containers or other devices to facilitate blood sampling. A hollow member 184 is also shown within the port 180. The hollow member 184 may have a sharp end to penetrate the seal of a blood draw container (see FIG. 28A).

The blood draw apparatus 1*c* also includes a flexible tube advancement handle 190. The flexible tube advancement handle 190 includes a lever 191 with an end 192 shaped to engage with the proximal end 197 of the flexible tube 195 and or the flexible tube seal 199. The flexible tube 195 has a distal end 196, a proximal end 197 and a flexible tube lumen 198. There is also a flexible tube seal 199 provided about the exterior of the flexible tube 195 to seal the flexible tube 195 within the nose section 7*a*.

Similar to the description above of the other devices, the blood draw device includes an access needle 20 extending through the housing lumen. The access needle 20 has an access needle lumen 23. The access needle 20 has a distal end that extends beyond the housing distal end, and a proximal end within the second interior volume portion 9*b*. As before, there is a guidewire 10 within the access needle lumen 23.

Other components in common with other devices include, for example, guide wire carrier 15, biasing element 33, release 30, guide wire lever 31, blood sensor 50 and indicator 51.

Figure 24B:
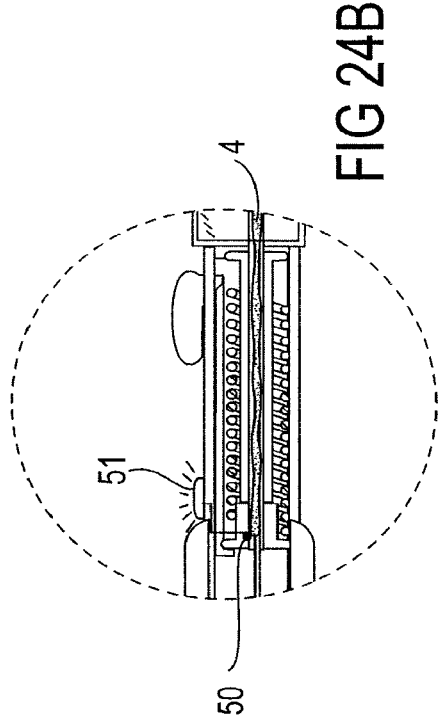
Figure 25:
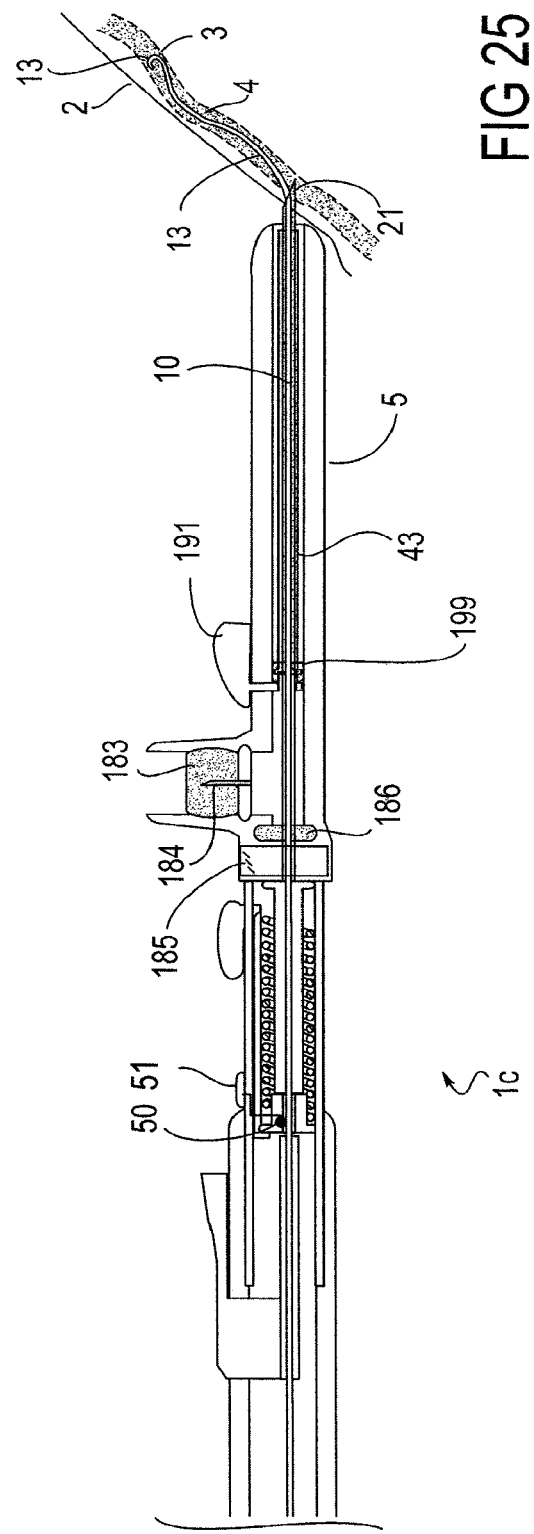
FIG. 25 illustrates the device as positioned in FIG. 24A after advancement of the guide wire into a vessel.
Figure 26:
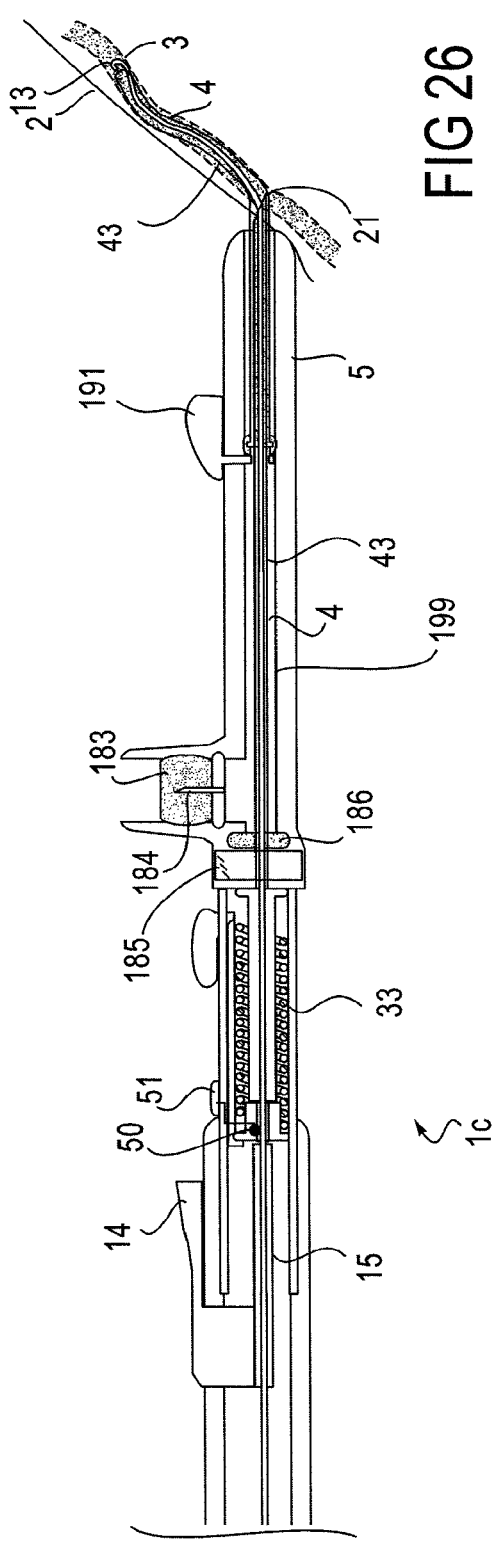
FIG. 26 illustrates the device as positioned in FIG. 25 after manual advancement of a catheter out of the housing and into the vessel over the guide wire.

FIG. 24A illustrates the blood draw device 1*c* during a conventional needle stick into a vessel 3 as described above and shown in FIG. 10. FIG. 24B, like FIG. 10A illustrates the detection of blood 4 within the needle lumen 23 and activation of the indicator 51. FIG. 25, like FIG. 11, illustrates the advancement of the guide wire tip 13 into the vessel 3. FIG. 26 illustrates the advancement of the flexible tube 195 into the vessel 3 in much the same way as the catheter advancement shown in FIG. 12 inserts the catheter into the vessel 3. The main difference here is that the flexible tube advancement handle 190 is provided for the distal movement of the flexible tube 195.

Figure 27:
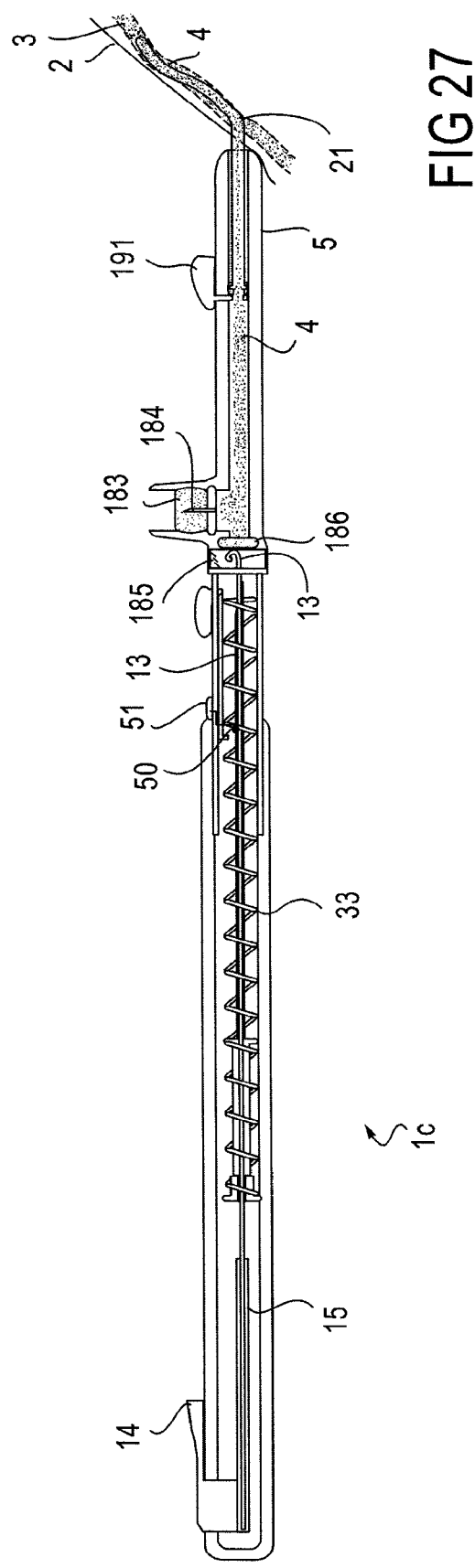
FIG. 27 illustrates the device of FIG. 26 after automatic withdrawal of the needle and guide wire into the housing to allow fluid communication from the vessel to the blood draw port and inspection of the guide wire tip in a tip view window.

With the flexible tube 195 within the vessel 3, the guide wire 10 and needle 20 may be withdrawn from the flexible tube 195 and the vessel 3 by activation of the release 30 (FIG. 27). Note that the needle 20 and the guide wire 10 are withdrawn to position a proximal to the seal 183. In this position, the needle 20 and the guide wire 10 are both within the second internal volume portion 9*b*. The flexible tube 195 now provides a fluid conduit from the vessel to the blood draw port 180.

Note that the guide wire tip 13 is visible in the view window 185. The housing may be formed from a clear, medical grade plastic that allows for easy inspection of the guide wire tip 13 if needed. The seal 186 closes once the needle 20 and guide wire 10 are withdrawn proximally into the housing 5. The seal 186 helps keep the blood within the housing near the blood sample port and the housing distal end.

FIG. 28A also shows the seal 186. The seal 186 allows the guide wire 10 and needle 20 to pass through as shown in FIG. 23A. When the guide wire and needle are withdrawn from the vessel (FIG. 27), the seal 186 closes and prevents blood from filling the proximal end of the housing. The needle and guidewire are withdrawn beyond it and it seals.

FIG. 28A illustrates how a blood draw container 182 and be placed on the blood draw port fixture 181. In this position, the hollow member 184 penetrates the seal 182*a* thereby allowing blood to be drawn into the container 182. When blood sampling is completed, the handle 190 is moved proximally thereby withdrawing the flexible tube 195 from the vessel 3 and into the nose section 7*a*. When the blood collection is completed, the device 1*c* is discarded.

Several alternative seal 186 designs are possible. FIGS. 28B and 28C illustrate a flap type seal where the flaps are distal facing (FIG. 28B) or proximal facing (FIG. 28C). In either orientation, the seals provide a blood tight seal around the needle during catheter insertion operations and then provide a blood tight seal within the housing once the needle and guidewire are withdrawn into the proximal end of the housing. It is to be appreciated that the various alternative seal embodiments in FIGS. 29A-33B and other seal embodiments described herein may be modified to provide distal facing or proximal facing sealing capabilities.

The seal 186 used to provide separation of the housing interior volumes may be provided using any suitable seal. Numerous sealing devices and configurations may be used as exemplified by the seal embodiments of FIGS. 28A-33B. The seal 186 and the alternatives described below are formed from a suitable flexible material such as rubber, silicone, or other medical grade elastomer that forms a suitable barrier to the passage of blood.

FIGS. 28B and 28C illustrate a seal 250 as an alternative embodiment to the seal 186. The seal 250 has flaps 250*a* and 250*b*. FIG. 28A is an embodiment where the flaps 250*a*, 250*b* are configured to draw together distally when the access needle 20 is withdrawn. FIG. 28C is an embodiment where the flaps 250*a* and 250*b* are configured to draw together proximally when the access needle 20 is withdrawn.

FIGS. 29A and 29B illustrate a sealing element 254 as an alternative embodiment to the seal 186. The sealing element 254 is attached to a base 251 that is configured to support the sealing element 254. The base 251 is sized to fit within the housing 5 and facilitate the use of sealing element 254 within the housing 5. The base 251 is used to mount the sealing element 254 within the housing to provide sealing capabilities like the seal 186 (see FIG. 27). The sealing element 254 has a nipple shape with an aperture 252. FIG. 29A illustrates the sealing configuration when the needle 20 is in use as in FIG. 26. When the needle 20 is in use, the aperture 252 forms a seal around the needle 20. FIG. 29B illustrates the sealing configuration of the sealing element 254 when the needle 20 is withdrawn into the housing. When the needle 20 is withdrawn proximal to the sealing element 254, the aperture 252 closes to function similar to seal 186 in FIG. 27.

FIGS. 30A and 30B illustrate a sealing element 256 as an alternative embodiment to the seal 186. The sealing element 256 is attached to a base 251 that is configured to support the sealing element 256. The base 251 is sized to fit within the housing 5 and facilitate the use of sealing element 256 within the housing 5. The base 251 is used to mount the sealing element 256 within the housing to provide sealing capabilities like the seal 186 (see FIG. 27). The sealing element 256 has a funnel shape with an aperture 252. FIG. 30A illustrates the sealing configuration when the needle 20 is in use as in FIG. 26. When the needle 20 is in use, the aperture 252 forms a seal around the needle 20. FIG. 30B illustrates the sealing configuration of the sealing element 256 when the needle 20 is withdrawn into the housing. When the needle 20 is withdrawn proximal to the sealing element 256, the aperture 252 closes to function similar to seal 186 in FIG. 27.

FIGS. 31A and 31B illustrate a sealing element 258 as an alternative embodiment to the seal 186. The sealing element 258 is separated into two parts 258a and 258b. The sealing element 258 is attached to a base 251 that is configured to support the sealing element 258. The base 251 is sized to fit within the housing 5 and facilitate the use of sealing element 258 within the housing 5. The base 251 is used to mount the sealing element 258 within the housing to provide sealing capabilities like the seal 186 (see FIG. 27). The sealing element parts 258a, 258b have a funnel shape and are biased together to form an aperture 252 similar to the sealing element 256. FIG. 31A illustrates the sealing configuration when the needle 20 is in use as in FIG. 26. When the needle 20 is in use, the parts 258a, 258b form an aperture 252 that seals around the needle 20. FIG. 31B illustrates the sealing configuration of the sealing element 258 when the needle 20 is withdrawn into the housing. When the needle 20 is withdrawn proximal to the sealing element 258, the parts 258a, 258b draw together to close the aperture 252 to function similar to seal 186 in FIG. 27.

FIGS. 32A and 32B illustrate a sealing element 260 as an alternative embodiment to the seal 186. The sealing element 260 is separated into two parts 260a and 260b. The sealing element 260 is attached to a base 251 that is configured to support the sealing element 260. The base 251 is sized to fit within the housing 5 and facilitate the use of sealing element 258 within the housing 5. The base 251 is used to mount the sealing element 260 within the housing to provide sealing capabilities like the seal 186 (see FIG. 27). The sealing element parts 260a, 260b have a flat shape like a duck bill and are biased together to form an aperture 252 similar to the sealing element 258. FIG. 32A illustrates the sealing configuration when the needle 20 is in use as in FIG. 26. When the needle 20 is in use, the parts 260a, 260b form an aperture 252 that seals around the needle 20. FIG. 32B illustrates the sealing configuration of the sealing element 258 when the needle 20 is withdrawn into the housing. When the needle 20 is withdrawn proximal to the sealing element 260, the parts 260a, 260b draw together to close the aperture 252 to function similar to seal 186 in FIG. 27.

FIGS. 33A and 33B illustrate a sealing element 262 as an alternative embodiment to the seal 186. The sealing element 262 is attached to a base 251 that is configured to support the sealing element 262. The base 251 is sized to fit within the housing 5 and facilitate the use of sealing element 262 within the housing 5. The base 251 is used to mount the sealing element 262 within the housing to provide sealing capabilities like the seal 186 (see FIG. 27). The sealing element 262 has an elongated tube 263 shape with an aperture 252 on the end of the tube 263. FIG. 33A illustrates the sealing configuration when the needle 20 is in use as in FIG. 26. When the needle 20 is in use, the aperture 252 forms a seal around the needle 20. FIG. 33B illustrates the sealing configuration of the sealing element 262 when the needle 20 is withdrawn into the housing. When the needle 20 is withdrawn proximal to the sealing element 262, the tube 263 collapses closing the aperture 252 thereby functioning similar to seal 186 in FIG. 27.

FIG. 34 illustrates a manual withdrawal blood draw device similar to the blood draw device illustrated and described in FIG. 23A. Unlike the embodiment of FIG. 23A, the blood draw device embodiment of FIG. 34 does not include any automatic guidewire withdrawal capabilities. Instead, the guide wire 10 is withdrawn by moving the guide wire handle 14 proximally until the guide wire tip 13 is visible proximal of the seal 186. The guide wire tip 13 may be visible in the view port 185. Similarly, the biasing element 33 has been replaced by a needle withdrawal handle 270 with a latch 272 having a fitting 273 that engages with the needle boss 24. Movement of the handle 270 moves the needle carrier 25 and in turn the needle 20.

FIG. 35 illustrates an alternative blood draw port 180 similar to that shown in FIG. 23A. Here, the hollow member 184 has been replaced by a puncture seal 183a. The puncture seal 183a allows for the use of a syringe and needle to penetrate the seal 183a to draw off a blood sample. This seal 183a is a suitable porous rubber or other material that would allow a user to inset a needle through the seal 183a and withdraw a sample from within the housing in the blood draw area.

FIG. 36 illustrates another alternative blood draw port 180 that is connected to a blood draw apparatus or fixture 292. The tubing 290 and the blood draw device 292 could be any convention blood draw device or other phlebotomy equipment. Here the blood draw fixture is modified into fixture 183a that seals with or receives the tubing 290. In this way, the blood draw device 292 is in communication with the interior volume to draw blood.

In contrast to the rigid housing tip and flexible tube used in FIG. 23A, there are also blood draw devices of the present invention that provide a flexible distal end. FIGS. 37A-42 illustrate an embodiment of one such flexible tip blood draw device 1d. As illustrated in the figures that follow, a pair of flexible tubes may be used to provide a flexible tip to the blood draw device.

FIG. 37A illustrates a section view of a blood draw device 1d. The blood draw device is similar to previous devices, such as that illustrated in FIG. 23A, and common references numbers are used.

FIG. 37A is an alternative of FIG. 23A where a flexible tube replaces the rigid distal end of the housing. In contrast to earlier embodiments, the flexible tube 195 is within an outer flexible tube 195 rather than the distal end of the housing. The flexible tube 195 has a distal end 196, a proximal end 197 and a flexible tube lumen 198. The proximal end 197 is sealed within housing 5 so that the lumen 198 is in communication with the first interior volume 9a. The outer flexible tube 380 includes an outer flexible tube distal end 381 and an outer flexible tube proximal end 382. The proximal end 382 may include a luer fitting, valve or a seal 386 held open while the inner flexible tube 195 is present. There is also an outer flexible tube lumen 383 that runs from the proximal end 382 to the distal end 381. Optionally, one or more flaps 384 are provided to secure or handle the outer flexible tube 380. In one embodiment, the outer flexible tube 380 is similar in construction to a catheter 40 described above.

As with other embodiments, there is provided an access needle 20, a guide wire 10, sensor 50, an indicator 51 and other similar components. As with other embodiments, the guide wire 10 is within the access needle lumen 23. The access needle 20 is within the lumens of the flexible tubes 195, 380. The flexible tube 195 is within the outer flexible tube lumen 198.

FIG. 37A illustrates the needle entering the vessel 3 and an indication of bleed back as discussed above. Next, FIG. 38 illustrates the advancement of the guide wire tip 13 into the vessel 3.

Figure 39:
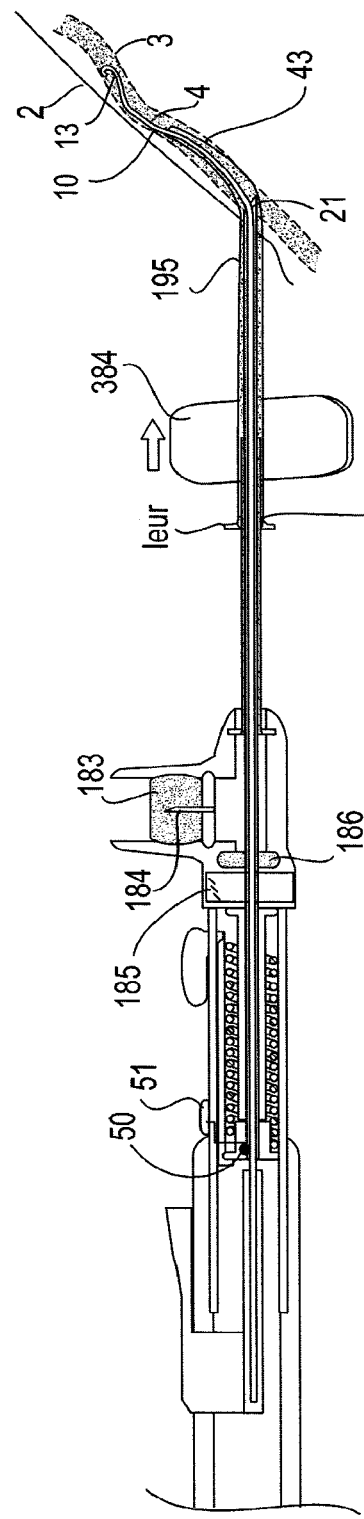
FIG. 39 illustrates the device as positioned in FIG. 38 after manual advancement of the outer flexible tubing along the inner flexible tubing and into the vessel over the guide wire.

FIG. 39 illustrates the advancement of the outer flexible tube 380 along the guide wire 10 and into the vessel 3. Note that the needle 10 is used to provide rigidity to allow the sliding of the tubes without kinking. Additionally, the outer tubing lumen 383 is sized to accommodate and slide along the outer wall of the inner tubing 195. The seal 386 maintains a seal between the flexible tubes.

Figure 40:
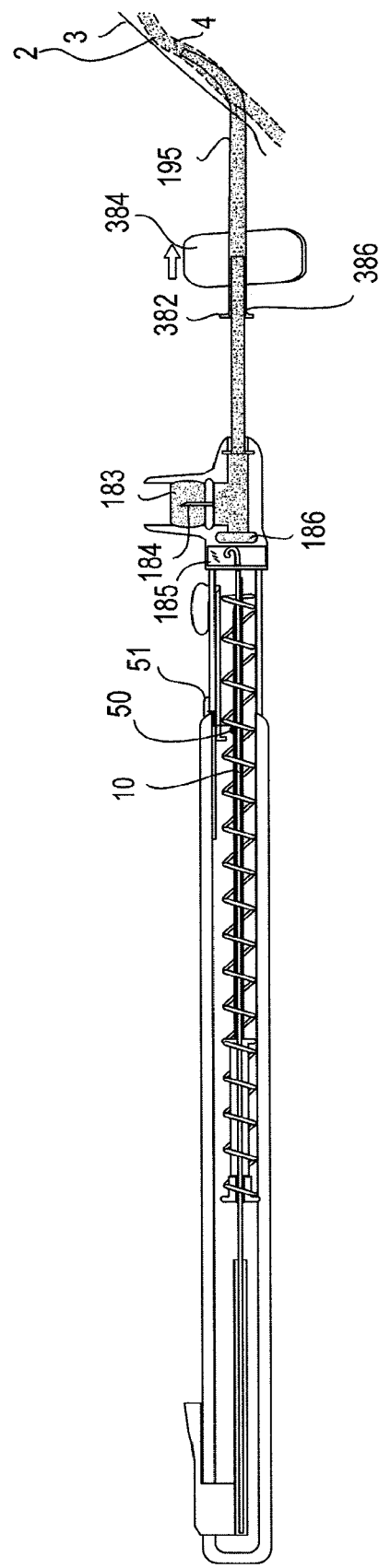
FIG. 40 illustrates the device as positioned in FIG. 39 after automatic withdrawal of the needle and guide wire into the housing to allow fluid communication from the vessel to the blood draw port and inspection of the guide wire tip in a tip view window. The figure also illustrates fluid communication from the vessel to the blood draw port using the inner and outer flexible tubes.
Figure 41:
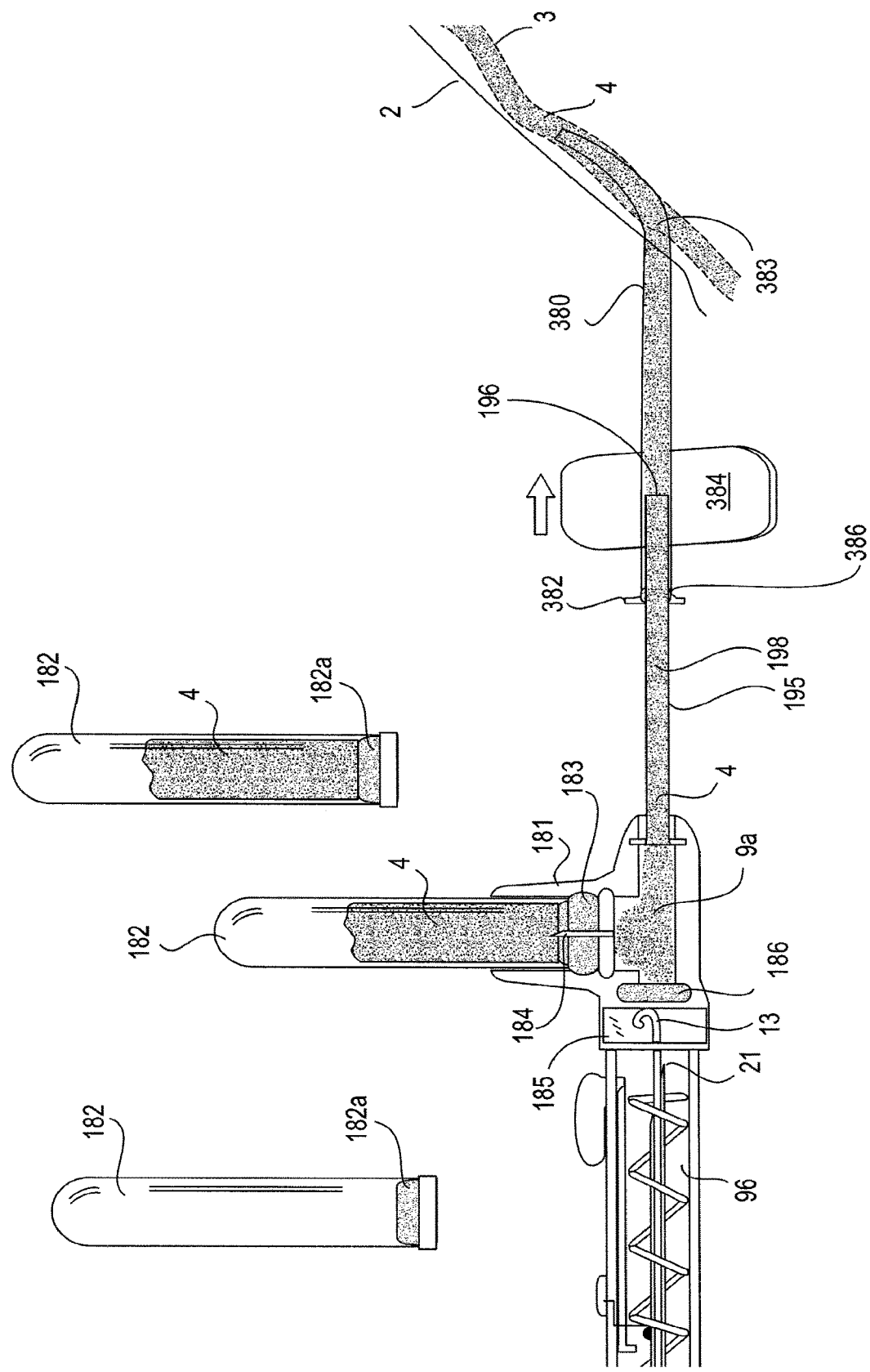
FIG. 41 illustrates an inserted blood draw device as positioned in FIG. 40 in use to draw blood samples.

FIG. 40 illustrates the withdrawal of the needle 20 and guide wire 10 as described above. Once the needle is removed, the flexible tubes provide fluid communication from the vessel 3 into the first interior volume 9*a*. One completed, the port 180 may now be used to draw blood as described above and shown in FIG. 41.

FIG. 42 illustrates the outer flexible tube remaining behind after completion of the blood draw. The outer tube may be a catheter hub with a seal or port on the proximal end. The seal or port 386 is held open by the inner flexible tube 195. Once the inner flexible tube 195 is removed, the seal 386 closes. The flexible tube device 380 could be used during hospital admissions for initial blood draw and then remain in place for use as an intravenous catheter. Also the device of FIG. 23A could be modified to accept a catheter 40 or hub 45 in the distal end of the housing, such as illustrated above. In this way, the placement of the flexible tube or cannula 380 for a blood draw is subsequently used as a catheter for further treatment of the patient.

Figure 43A:
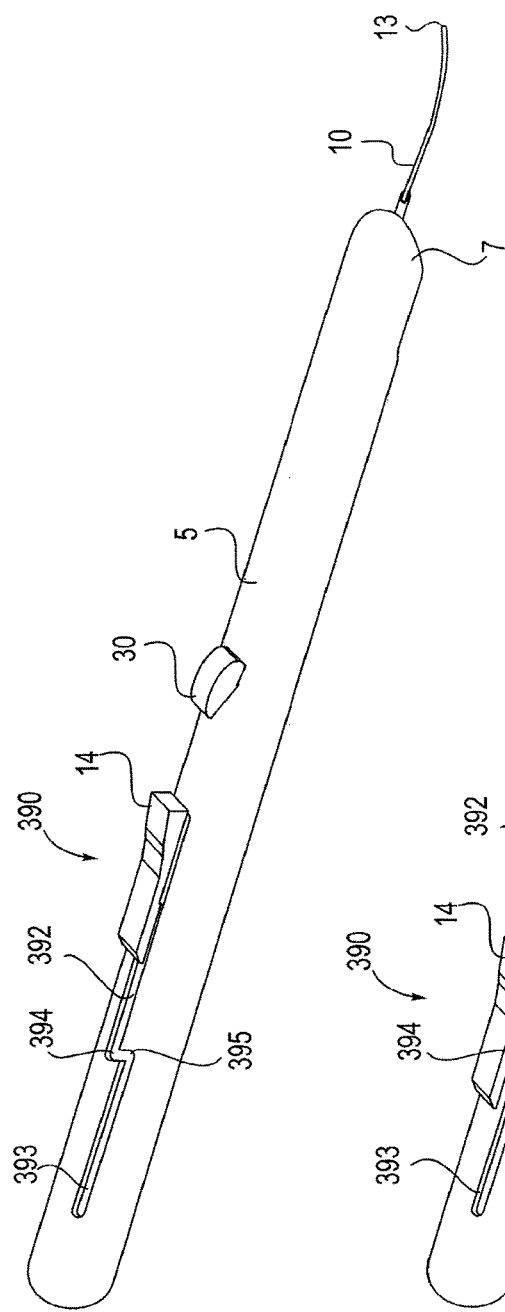
FIG. 43A-43C are isometric views of an insertion device with guide wire tip inspection capabilities where
Figure 43B:
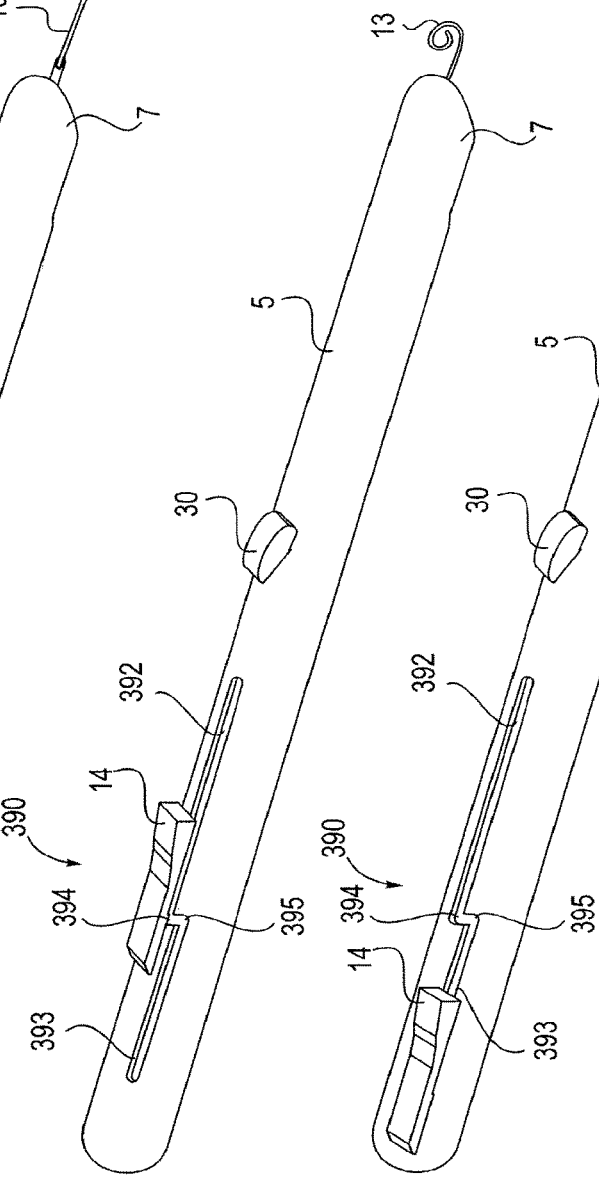
Figure 43C:
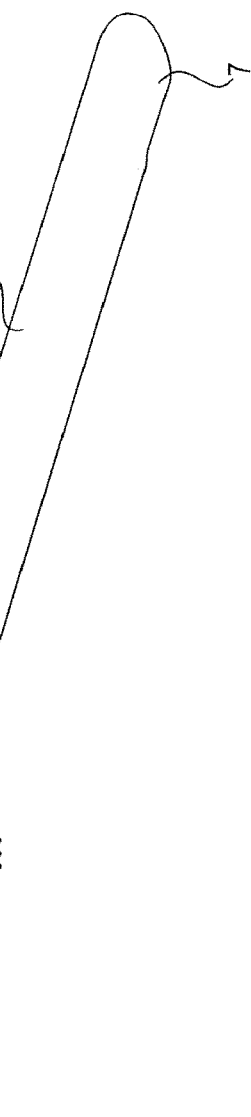

FIG. 43A-43C shows another form of mechanical stop to allow for inspection of the guidewire tip. This housing 5 includes a shaped slot 390 that hinders the movement of the guide wire handle 14 to facilitate inspection of the guide wire tip 13. The shaped slot 390 has a proximal portion 392 and a distal portion 393. A notch 394 is position proximal to the distal portion 392. A by pass 395 allows movement of the guide wire handle 14 beyond the notch 394 and to proceed into the proximal slot portion 393.

FIG. 44A-44F illustrate another alternative venous access device that provides a mechanical stop to facilitate inspection of the guide wire tip 13. Insertion device 1*d* is shown during an insertion process similar to those devices above. At this point, the catheter advancement lever 550 has advanced the intravenous catheter 40 along slot 8 in the distal end of housing 5. The guidewire tip 13 and the catheter distal end 42 are visible in the vessel 3. The insertion device includes a bleed back notch 501 in the access needle 20. A needle stop 505 is positioned within the housing interior space 9 to support the needle carrier 25 and hold the bias element 33 in compression against the release button 30. The guide wire lever 14 and guide wire carrier 15 are shown in a distal most position against the guide wire stop 510. The guide wire stop 510 can be used to stop distal advancement of the guide wire carrier 15 so that the guide wire carrier does not interfere with the position of the release button 30 or the needle carrier boss 24. Additionally, as best seen in FIG. 44E, the height of the guide wire stop 510 and the proximal wedge 540 are selected to prevent the distal movement of the post fracture inspection stop 515.

Returning to FIG. 44A, the guide wire carrier 15 also includes an inspection stop 515. The inspection stop 515 includes a fracture point 520 and a tip 525. The fracture point 520 is positioned to allow the tip 525 to break away from the inspection stop 515. The insertion device 1*d* also includes a housing stop 530. The housing stop 530 includes a distal wedge 535 and a proximal wedge 540. The distal wedge 535 is sized and positioned to interact with and cause the fracture of the tip 525. The size and shape of the proximal wedge 540 is intended to prevent the distal movement of the guide wire carrier once the carrier has moved into a position proximal to the proximal wedge 540 (see FIG. 44F).

The operation of the insertion device 1*d* to permit guide wire tip inspection will now be described. FIG. 44A illustrates the insertion device 1*d* at the point of catheter insertion just before withdrawal of the guide wire 10 and access needle 20. FIG. 44B illustrates the automatic withdrawal of the guide wire 10 and access needle 20 by lifting/operating the release button 30. After the biasing element 33 expands, the guide wire carrier 15 is moves proximally until the tip 525 contacts the distal wedge 535. At this point, the catheter 40 is removed from the housing 1*d* and attached to the patient. FIG. 44C illustrates the insertion device 1*d* once the catheter 40 is removed. FIG. 44D is a bottom up view of the device 1*d* shown in FIG. 44C. FIG. 44D illustrates that while the inspection stop 515 remains in contact with the distal wedge 535, the guide wire tip 13 and, optionally, the access needle tip 21 are visible in housing distal end 7 within the interior volume 9 as is with the catheter. FIG. 44D illustrates the insertion device 1*d* once the guide wire tip inspection is complete.

After inspecting the guide wire tip 13, a user may advance the guide wire carrier 15 proximally. The proximal movement of the guide wire carrier 15 urges the inspection stop 515 against the distal wedge 525 until the tip 525 separates from the inspection stop 515 along the fracture point 520. Thereafter, the guide wire carrier 15 moves proximally beyond the proximal wedge 540. The proximal movement of the guide wire carrier 15 withdraws the access needle 20 and the guide wire tip 13 into the housing interior space 9 (FIGS. 44E and 44F).

While many of the above embodiments are illustrated and described with a catheter 40 having a hub or wings 45, embodiments of the present invention are not so limited. Any style catheter may be used with the insertion and blood draw devices described herein. Catheters without hubs or wings or butterfly style catheters may also be used with the devices and techniques described herein.

What is claimed is:

1. A catheter insertion device, comprising:
   a handle having a proximal region and a distal region, the distal region including a slot between a top extension and a bottom extension, the slot extending through a distal end of the distal region;
   a needle having a proximal end positioned in the proximal region of the handle and a distal end extending from the distal region of the handle;
   a guide wire having a proximal end positioned in the proximal region of the handle and a distal end positioned in a lumen of the needle; and
   a catheter positioned coaxially over the needle, the catheter having a proximal end connected to a catheter hub, the catheter hub slidably disposed in the slot to enable movement from a first position in the distal region of the handle to a second position distal of the distal region.

2. The catheter insertion device according to claim 1, further comprising a guide wire advancement member coupled to the proximal end of the guidewire, wherein movement of the guide wire advancement member moves the guide wire relative to the needle.

3. The catheter insertion device according to claim 2, wherein the guide wire advancement member includes a guide wire actuator connected to a guide wire carrier, the guide wire actuator accessible outside of the handle, the guide wire carrier coupled to the guide wire in the proximal region of the handle.

4. The catheter insertion device according to claim 3, wherein movement of the guide wire actuator relative to the handle moves the guide wire relative to the needle.

5. The catheter insertion device according to claim 1, wherein the distal end of the guide wire comprises a coiled tip.

6. The catheter insertion device according to claim 1, wherein the catheter has a distal end extending from the distal region of the handle in the first position.

7. The catheter insertion device according to claim 1, wherein the catheter hub is coupled to a catheter actuator, and wherein movement of the catheter actuator relative to the handle transitions the catheter hub from the first position to the second position.

8. The catheter insertion device according to claim 1, wherein the catheter comprises a seal.

9. The catheter insertion device according to claim 1, wherein the proximal region of the handle includes an enclosed interior space.

10. The catheter insertion device according to claim 1, wherein the proximal region of the handle includes a seal, the needle extending through the seal in the first position, the seal closing upon movement of the distal end of the needle into the proximal region of the handle proximal of the seal.

11. The catheter insertion device according to claim 10, wherein the seal includes a plurality of flaps.

12. The catheter insertion device according to claim 10, wherein the seal is attached to a base designed to mount the seal in the proximal region of the handle.

13. The catheter insertion device according to claim 1, wherein the proximal end of the needle is designed to move relative to the handle.

14. The catheter insertion device according to claim 13, further comprising:
- a needle carrier connected to the proximal end of the needle;
- a biasing element surrounding the needle carrier; and
- an actuating member holding the biasing element in a compressed configuration.

15. The catheter insertion device according to claim 14, wherein actuation of the actuating member enables the biasing element to expand to an expanded configuration, resulting in proximal movement of the needle carrier in the proximal region of the handle.

16. The catheter insertion device according to claim 15, wherein the proximal movement of the needle carrier results in proximal movement of the guide wire relative to the handle.

17. The catheter insertion device according to claim 1, wherein the catheter hub comprises a pair of laterally extending wings.

18. The catheter insertion device according to claim 17, wherein opposing ends of the pair of laterally extending wings extend laterally out of the slot.

* * * * *